(12) United States Patent
Murad et al.

(10) Patent No.: US 10,905,651 B1
(45) Date of Patent: Feb. 2, 2021

(54) ZEINMERSOME NANOCARRIERS FOR DRUG DELIVERY TO THE LIVER

(71) Applicant: King Abdulaziz University, Jeddah (SA)

(72) Inventors: Hussam Aly Sayed Murad, Jeddah (SA); Osama Abdelhakim Aly Ahmed, Jeddah (SA); Usama Ahmed Fahmy Ahmed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/944,949

(22) Filed: Jul. 31, 2020

(51) Int. Cl.
| | | |
|---|---|---|
| A61K 9/127 | (2006.01) | |
| A61K 47/34 | (2017.01) | |
| A61K 49/00 | (2006.01) | |
| A61P 1/16 | (2006.01) | |
| A61K 31/4178 | (2006.01) | |

(52) U.S. Cl.
CPC ........ *A61K 9/1272* (2013.01); *A61K 31/4178* (2013.01); *A61K 47/34* (2013.01); *A61K 49/0008* (2013.01); *A61P 1/16* (2018.01)

(58) Field of Classification Search
CPC .... A61K 9/1272; A61K 49/008; A61K 47/34; A61K 31/4178; A61P 1/16
See application file for complete search history.

(56) References Cited

PUBLICATIONS

Nitta et al, Biopolymer-Based Nanoparticles for Drug/Gene Delivery and Tissue Engineering, International Journal of Molecular Sciences, 14, p. 2929-2964. (Year: 2013).*

* cited by examiner

*Primary Examiner* — Carlos A Azpuru
(74) *Attorney, Agent, or Firm* — W & C IP

(57) ABSTRACT

Zeinmersomes (ZMS) comprising zein, a phospholipid and a PEG-polymer are formulated to encapsulate a drug of interest. Olmesartan medoxomil (OM) is encapsulated in the ZMS (OM-ZMS) for oral administration and taken up by the liver where OM diffuses from the ZMS nanocarrier. OM concentrations in liver were at least 8 times higher than that measured in plasma. Established fibrosis was reversed in a thioacetamide-induced rat model of human chronic hepatic fibrosis. The OM-ZMS provides a hepatic drug delivery system that reduces the potential of side-effects caused by OM, including OM-associated sprue-like enteropathy, to treat chronic hepatic fibrosis and associated duodenal changes.

5 Claims, 12 Drawing Sheets
(10 of 12 Drawing Sheet(s) Filed in Color)

2A

2B

5A

5B

6A

6B

ZEINMERSOME NANOCARRIERS FOR DRUG DELIVERY TO THE LIVER

BACKGROUND OF THE INVENTION

Field of the Invention

The invention generally relates to a pharmaceutical composition comprising nanocarriers for drug delivery to the liver. The invention further relates to methods of formulating nanocarriers encapsulating a drug of interest, and methods of administration of drug-loaded nanocarriers to treat, prevent or reverse a liver disease or condition, particularly chronic hepatic fibrosis and associated duodenal changes.

Background

Liver cirrhosis is a major cause of morbidity and mortality globally. Liver fibrosis occurs as a protective process in response to acute or chronic liver injury, but prolonged fibrotic process leads to massive accumulation of extracellular matrix (ECM) components that inhibits regeneration of hepatocytes and leads to permanent liver damage. The nonparenchymal cells such as the immune cells and hepatic stellate cells (HSCs) have essential roles in liver fibrosis. Activated HSCs express α-smooth muscle actin and produce excessive amounts of collagen and other ECM components during fibrogenesis. Mild to moderate fibrosis is reversible, but severe fibrosis is irreversible and can cause liver decompensation, cirrhosis and end-stage liver disease. In some cases, chronic fibrosis may lead to hepatocellular carcinoma.

The inflammatory response after tissue injury occurs as acute and late phases; fibrosis starts to form in the late phase. Tumor necrosis factor-α (TNF-α) and transforming growth factor-β (TGF-β) are key fibrogenic cytokines in the liver. Acute phase inflammation can be controlled to some degree with non-steroidal anti-inflammatory drugs (NSAIDs). In the late phases, corticosteroids inhibit expression of the fibrotic genes in the HSCs and reduce ECM deposition, but they also suppress immune cell infiltration and aggravate liver injury. Thus, the usefulness of corticosteroids as an anti-fibrotic treatment is limited.

During liver fibrogenesis, the activated HSCs express the renin angiotensin system (RAS), angiotensin II type 1 (ATI) receptors, and α-smooth muscle actin. They synthesize angiotensin II (AT II) which promotes inflammation and production of collagen and other components of the ECM. The angiotensin converting enzyme inhibitors (ACEIs) and the AT1 receptor blockers (ARBs) have been shown to reduce the progression of liver fibrosis in vivo and were used for treatment of patients with portal hypertension with very promising hemodynamic results. Use of nanoparticles as carriers for antifibrotic drugs to target receptors expressed or over-expressed by the active HSCs allows accumulation of high concentrations in the liver and maximum efficacies in treatment of liver fibrosis and also minimize associated side effects compared to the standard drugs (Giannitrapani et al. 2014; *World J Gastroent* 20(23):7242).

Currently, there is no standard therapy for liver fibrosis. Many agents have shown potent anti-fibrotic effects in vitro, but these exert only minor effects in vivo due to failure to achieve sufficient concentrations around the HSCs. In addition, these agents have had adverse effects due to off-target effects on non-target cells.

Based on unique pharmacological profile, olmesartan medoxomil (OM) has received a great attention (Kellici et al. 2016; *Arab J Chem* 12(8) online). However, OM was reported to be the cause of sprue-like enteropathy in 22 cases diagnosed at the Mayo Clinic over a three-year period. The enteropathy was manifested with severe chronic diarrhea with significant weight loss sometimes requiring hospitalization. The mechanism is unclear, but it may be a cell-mediated or local delayed hypersensitivity reaction. In contrast, no link was identified between OM use and occurrence of gastrointestinal disease in the Randomised Olmesartan and Diabetes Microalbuminuria Prevention (ROADMAP) study conducted on a total of 2232 patients treated for about three years with OM (40 mg/day). While the sprue-like enteropathy is a rare occurrence, the possibility of gastrointestinal disease as a side effect of OM remains (Menne et al. 2012; *Mayo Clin Proceed*: Elsevier). Thus, the FDA warns against this olmesartan medoxomil-associated sprue-like enteropathy, and the olmesartan medoxomil label lists diarrhea as a side effect. Thus, there is a need for an antifibrotic therapy for chronic hepatic fibrosis with acceptable efficacy and safety profiles.

SUMMARY OF THE INVENTION

The invention is a pharmaceutical composition comprising nanocarriers for drug delivery. While any suitable drug may be used in practicing the invention, an exemplary drug is olmesartan medoxomil. The invention is also a method of formulation of nanocarriers loaded with a drug, and a method of administration to a subject. An exemplary subject is one who is suffering from established or chronic hepatic fibrosis, or from duodenal changes associated with hepatic fibrosis.

In on embodiment, the invention is a pharmaceutical composition comprising a drug encapsulated in a zeinmersome nanocarrier. The zeinmersome (ZMS) comprises a mixture of zein, an amphiphilic copolymer and at least one phospholipid. The zein, amphiphilic copolymer and phospholipid form a lipid bilayer encapsulating the drug. In an exemplary embodiment, the drug is olmesartan, olmesartan medoxomil or Benicar. Olmesartan medoxomil (OM) is typically in present in the ZMS at a concentration in the range of 3% to 15% w/w. The size range of the ZMS is typically within the range of 95 to 200 nm in diameter. Thus, OM is carried in a nanosized ZMS vesicle bounded by the lipid bilayer.

The amphiphilic copolymer is polyethylene glycol (PEG) conjugated to a polymer, such as a methyl ether-block-poly (lactide-co-glycolide) (PLGA), or PEG-PLGA. The phospholipid is at least one selected from the group consisting of phosphatidylcholine, phosphatidic acid, phosphatidylethanolamine, phosphatidylserine, phosphatidylglycerol, phosphatidylinositol, phosphatidylinositol phosphate, phosphatidylinositol bisphosphate and phosphatidylinositol trisphosphate. In one embodiment, the phospholipid is phosphatidylcholine.

In another embodiment, the invention is a method for preparing the ZMS for delivery of an encapsulated drug to liver cells in a subject, comprising the steps of
dissolving suitable amounts of the drug and phosphatidylcholine in ethanol in a first solution;
dissolving suitable amounts of zein and polyethylene glycol-polylactic acid-co-glycolic acid (PEG-PLGA) in ethanol in a second solution;
combining the first solution and the second solution;
evaporating the combined first and second solutions until the drug, the phosphatidylcholine, the zein and the PEG-PLGA form a solid;

adding deionized water and allowing the solid to become hydrated and form vesicles;

sonicating the vesicles at an appropriate amplitude for a suitable period of time to yield ZMS in the nanosized range; and, optionally lyophilizing the ZMS for storage under nitrogen.

In an exemplary method for preparing drug-loaded ZMS vesicles, the drug is OM.

In still another embodiment, the invention is a method for treating and/or reversing chronic hepatic fibrosis in a subject in need thereof, comprising the steps of preparing OM-ZMS and administering a therapeutically effective quantity of the OM-ZMS to the subject. The ZMS comprise a mixture of zein, an amphiphilic copolymer and at least one phospholipid; encapsulating a suitable amount of OM within a nanosized vesicle bounded by the lipid bilayer (OM-ZMS) in a pharmaceutically acceptable carrier, administering a therapeutically effective quantity of the OM-ZMS to the subject. In an exemplary embodiment of the method for treating and/or reversing chronic hepatic fibrosis, the phospholipid is the amphiphilic copolymer is polyethylene glycol-polylactic acid-co-glycolic acid (PEG-PLGA) and the at least one phospholipid is phophatidylcholine.

While other routes of administration are contemplated, the ZMS of the invention may be administered orally to the subject. The ZMS are preferentially taken up by hepatic cells from the blood when they pass through vasculature of the liver. Thus, hepatic uptake of OM-ZMS results in a higher concentration of free olmesartan in liver than in plasma. A therapeutically effective dose typically is achieved when the ratio of hepatic/plasma concentration of free olmesartan is greater than 8. In one embodiment, free olmesartan plasma concentration in a treated subject remains lower than 5 ng/ml and a ratio of free olmesartan hepatic/plasma concentrations in the range of 8 to 12.

In some embodiments of the method of treatment, the subject is a human who is suffering from one or more hepatic disease or condition associated with fibrosis, such as cirrhosis, hepatocellular carcinoma, nonalcoholic fatty liver, hepatitis B, hepatitis C, autoimmune hepatitis, primary biliary cholangitis, primary sclerosing cholangitis, alpha-1 antitrypsin deficiency, hemochromatosis, Wilson disease, Budd-Chiari syndrome, heart failure, portal vein thrombosis, veno-occclusive disease of the liver, congenital hepatic fibrosis, or liver damage caused by alcohol and/or drug abuse.

In another embodiment, the subject is a rat that has been chemically treated with a substance, such as thioacetamide (TAA), to induce hepatic fibrogenesis as a model of chronic hepatic fibrosis in humans for testing efficacy of a drug of interest. The TAA is administered to the rat in a sufficient amount and for a suitable time period to promote fibrogenesis until reaching a preplanned stage of disease, so that the condition mimicking human chronic hepatic fibrosis is already established prior to treatment with any drug of interest, which may be a therapeutically effective amount of OM-ZMS. Thus, the rat model of "already-established" chronic hepatic fibrosis can be used to study the effects of hepatic fibrosis, such as morphological changes in the duodenum associated with hepatic fibrosis, as well as responses to treatment with known or investigational therapeutic drugs.

A therapeutically effective amount of the pharmaceutical composition of the invention is that which is sufficient to reduce or improve at least one pathophysiological symptom of hepatic fibrosis, such as deposition of abnormal extracellular matrix; deposition of excessive extracellular matrix; aggregation of Kupffer cells, platelets, and/or leukocytes; elevated levels of inflammatory cytokines; elevated levels of growth factors; and/or portal hypertension. The pathophysiological symptom may also be one associated with hepatic fibrosis but occurring in the duodenum, including edema, vascular congestion, increased cellular infiltration, irregularly distributed microvilli and distorted microvilli.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are incorporated in and constitute a part of this specification, illustrate embodiments of the invention and, together with a general description of the invention given above, and the detailed description given below, serve to explain the invention.

FIG. 2A) shows the size distribution of the nanoparticles; and FIG. 2B) shows zeta potential of the nanoparticles.

DETAILED DESCRIPTION

Figure 1:
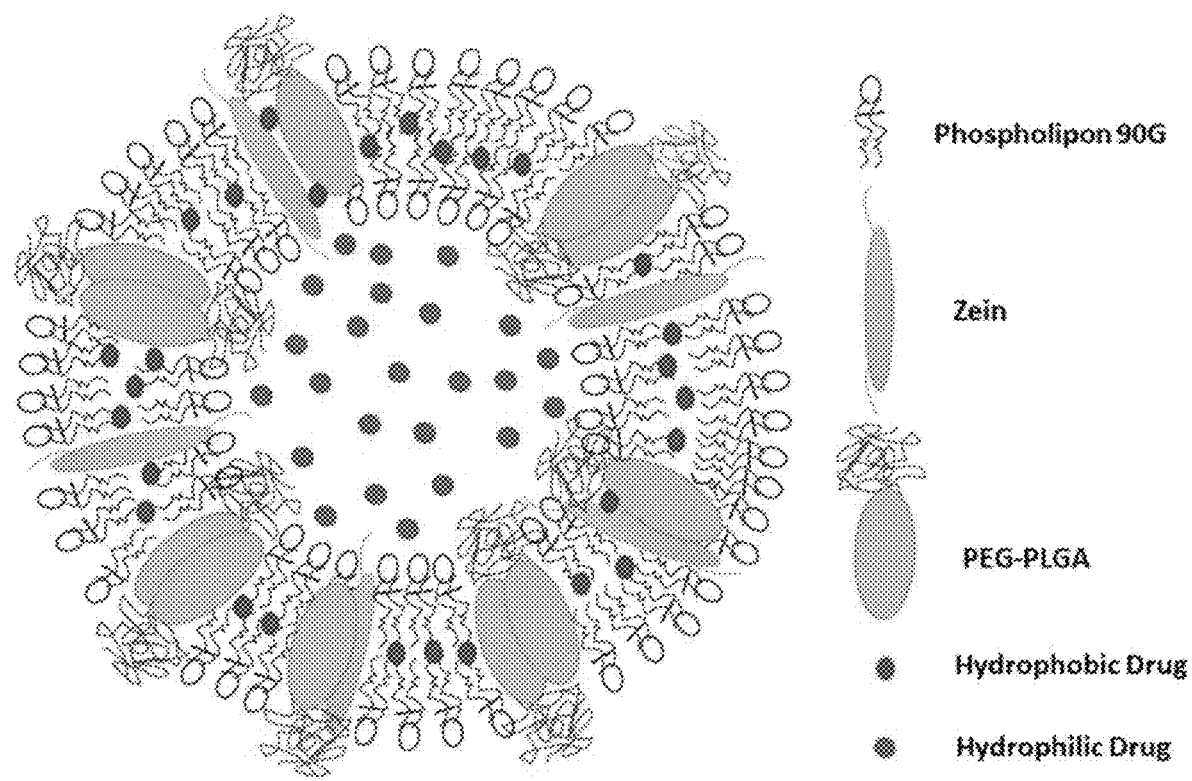
FIG. 1 shows a diagram of a zeinmersome structure, comprising a bilayer membrane of amphipathic phospholipids (Phospholipon 90G), PEG-polymers (PEG-PLGA) and zein molecules. The zeinmersome sphere can encapsulate and carry a hydrophilic drug (circles) in the central core area, and/or a hydrophobic drug (ovals) within the hydrophobic area within the bilayer membrane.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

The invention is a pharmaceutical composition comprising zein and amphipathic molecules that self-assemble into a bilayer membrane able to encapsulate a drug of interest in a specialized liposome called a zeinmersome (ZMS). Exemplary amphipathic molecules that may be use are a phospholipid, such as phosphatidylcholine, and PEG-PLGA, a biologically compatible polymer.

As used herein, the terms "zeinmersome" and "ZMS" are used interchangeably for the nanoparticles or nanocarriers of the invention. The ZMS nanocarriers have a basic structure known in the art as liposomes or vesicles. As with other types of liposomes and vesicles, the zeinmersomes comprise a lipid bilayer that self-assembles by forming a membrane structure of polar molecules surrounding a central core area. Hydrophobic regions are partitioned within the bilayered membrane formed by the polar molecules. Hydrophilic regions are excluded from the hydrophobic zone within the bilayer and thus are partitioned to the inner core within the inner face of the bilayered membrane. Inclusion of the hydrophobic zein molecules in the formulation confers both novelty and the name to the nanocarrier of the invention.

As used herein, the terms "amphipathic" and "amphiphilic" are used interchangeably to describe the polar molecules forming the bilayer membrane of the ZMS.

While any suitable drug may be used in practicing the invention, one embodiment of the invention comprises a drug known as olmesartan medoxomil. Olmesartan medoxomil (OM) is a non-peptide angiotensin AT II receptor blocker as an oral administration formulation that is FDA-approved for the treatment of hypertension, heart failure and diabetic kidney disease under the trade name Benicar, among others. The generic is also marketed worldwide under various names such as Olmetec, Benitec, Erastapex, Olarbi, Olmat, Olmax, Olmecip, Olmesafe, Olmesar, Olmetime, Olmetor, Olmetrack, Olmzest, Olmighty, Olmitop, Olsar, Olsavas, Olways, Pinom, Winbp, Zoltab, Golme, Votum. The IUPAC name for OM is (5-methyl-2-oxo-1,3-dioxol-4-yl)methyl 5-(2-hydroxypropan-2-yl)-2-propyl-3-[[4-[2-(2H-tetrazol-5-yl)phenyl]phenyl] methyl]imidazole-4-carboxylate. Other formulations of OM in multi-drug combinations, such as olmesartan/hydrochlorothiazide or olmesartan/amlodipine, are known and are contemplated for practicing the invention.

When OM is formulated in ZMS (OM-ZMS) and administered according to the methods of the invention, circulating OM-ZMS are preferentially taken up by the liver where the hepatic concentration of OM increases compared to plasma concentration and the OM effectively reverses chronic fibrosis.

As used herein, the terms "raw" OM and "free" OM refer to OM that is not encapsulated in OM-ZMS. In general, raw OM refers to the non-encapsulated form that is available for administration to a patient, while free OM refers to OM that may have been encapsulated, but has diffused from the ZMS, or has been released from disrupted OM-ZMS.

In one embodiment, the invention is a pharmaceutical composition comprising a drug encapsulated in a zeinmersome nanocarrier. The zeinmersome (ZMS) comprises a mixture of zein, an amphiphilic copolymer and at least one phospholipid. The zein, amphiphilic copolymer and phospholipid form a lipid bilayer encapsulating the drug. In an exemplary embodiment, the drug is olmesartan, olmesartan medoxomil or Benicar. Olmesartan medoxomil (OM) is typically in present in the ZMS at a concentration in the range of 3% to 15% w/w. The size range of the ZMS is typically within the range of 95 to 200 nm in diameter, with an average size in the range of 120 nm to 150 nm, and typically 130 nm to 140 nm. Thus, the drug is carried within a nanosized ZMS vesicle having a size greater than those known to be rapidly cleared by the kidneys and smaller than those cleared by cells and tissues of the reticuloendothelial system. Thus, the ZMS are optimally sized to be "cleared" by the liver and then deliver an encapsulated drug directly to hepatic tissues.

In one embodiment, the amphiphilic copolymer is polyethylene glycol (PEG) conjugated to a polymer, such as a methyl ether-block-poly (lactide-co-glycolide) (PLGA), or PEG-PLGA. PEG is a synthetic polyether that is commercially available in a range of molecular weights. These polymers are amphiphilic and soluble in water as well as in many organic solvents (e.g., methylene chloride, ethanol, toluene, acetone, and chloroform). PEG has been found to be nontoxic and is approved by the FDA for use as a carrier in pharmaceutical formulations, such as embodiments of the invention. Most PEGs with $M_W<1,000$ are rapidly removed from the body unaltered with clearance rates inversely proportional to polymer molecular weight.

In one embodiment, the phospholipid is phosphatidylcholine. The phosphatidylcholine can be a commercially available preparation such as Phospholipon® (American Lecithin Company; Oxford Conn.) at varying degrees of purity. In exemplary embodiment, the phosphatidylcholine is Phospholipon®90G, comprising pure phosphatidylcholine stabilized with 0.1% ascorbyl palmitate is a form suitable for use in a pharmaceutical composition. Preparations of other phospholipids are known in the art and can be substituted for phosphatidylcholine. Thus, the phospholipid can be any one of phosphatidylcholine, phosphatidic acid, phosphatidylethanolamine, phosphatidylserine, phosphatidylglycerol, phosphatidylinositol, phosphatidylinositol phosphate, phosphatidylinositol bisphosphate and phosphatidylinositol trisphosphate, or a mixture thereof.

In another embodiment, the invention is a method for preparing the ZMS for delivery of an encapsulated drug to liver cells in a subject, comprising the steps of
dissolving suitable amounts of the drug and phosphatidylcholine in ethanol in a first solution;
dissolving suitable amounts of zein and polyethylene glycol-polylactic acid-co-glycolic acid (PEG-PLGA) in ethanol in a second solution;
combining the first solution and the second solution;
evaporating the combined first and second solutions until the drug, the phosphatidylcholine, the zein and the PEG-PLGA form a solid;
adding deionized water and allowing the solid to become hydrated and form vesicles;
sonicating the vesicles at an appropriate amplitude for a suitable period of time to yield ZMS in the nanosized range; and, optionally
lyophilizing the ZMS for storage under nitrogen.

In an exemplary embodiment of the method for preparing drug-loaded ZMS vesicles, the drug is OM. An exemplary subject is one who is suffering from established or chronic hepatic fibrosis, or from duodenal changes associated with hepatic fibrosis.

In still another embodiment, the invention is a method for treating and/or reversing chronic hepatic fibrosis in a subject in need thereof, by providing a formulation of OM-ZMS in a pharmaceutically acceptable carrier and administering a therapeutically effective quantity of the OM-ZMS to the subject. While other routes of administration such as intraperitoneal and intravenous are contemplated, the ZMS of the invention may be administered orally to the subject. Ability to deliver the OM-ZMS orally also increases the utility of the treatment, since it may be administered outside the clinic setting.

The nanoformulation of OM-ZMS has an improved efficacy against hepatic fibrosis when compared to OM alone. The OM-ZMS has a higher oral bioavailability, a higher concentration in liver, and a more efficient reduction of fibrotic hepatic changes compared with the standard formulation of OM. Additionally, the nanoformulation of OM-ZMS allows a therapeutically effective dose of OM to accumulate in the liver, while maintaining a lower concentration in the blood. A key benefit of the invention is that it provides a formulation that potentially reduces the risk of side effects that have accompanied OM treatments. In March 2013, the FDA issued a statement to warn against olmesartan medoxomil-associated sprue-like enteropathy. This side effect is rare and generally improves after stopping the drug. The mechanism is thought to be a cell-mediated or local delayed hypersensitivity reaction, but the precise cause is not known. In any case, the possibility of serious side effects exists with oral administration of OM or Benicar, and the OM-ZMS of the invention provide a treatment that avoids induction of olmesartan medoxomil-associated sprue-like enteropathy.

The typical concentration of OM in the OM-ZMS is in the range of 3% to 15% w/w. The OM-ZMS are preferentially taken up by hepatic cells when they pass through the liver and OM diffuses from the ZMS, resulting in a higher concentration of free olmesartan in liver compared to the concentration remaining in the blood. A therapeutically effective dose typically has been achieved when ratio of hepatic/plasma concentration of free olmesartan is greater than 8. In one embodiment, free olmesartan plasma concentration in a treated subject is lower than 5 ng/ml and a ratio of free olmesartan hepatic/plasma concentrations in the range of 8 to 12. These plasma and hepatic levels can be achieved with OM-ZMS doses in the range of 1 to 16 mg/kg/day, 1 to 10 mg/kg/day, 2 to 8 mg/kg/day, or 2 to 4 mg/kg/day.

In some embodiments of the method of treatment, the subject is a human who is suffering a hepatic disease or condition such as cirrhosis, hepatocellular carcinoma, non-alcoholic fatty liver, hepatitis B, hepatitis C, autoimmune hepatitis, primary biliary cholangitis, primary sclerosing cholangitis, alpha-1 antitrypsin deficiency, hemochromatosis, Wilson disease, Budd-Chiari syndrome, heart failure, portal vein thrombosis, veno-occclusive disease of the liver, congenital hepatic fibrosis, or who is suffering from liver damage caused by alcohol and/or drug abuse. The therapeutically effective amount is that which is sufficient to reduce or improve at least one pathophysiological symptom of hepatic fibrosis, such as deposition of abnormal extracellular matrix; deposition of excessive extracellular matrix; aggregation of Kupffer cells, platelets, and/or leukocytes; elevated levels of inflammatory cytokines; elevated levels of growth factors; and portal hypertension.

In addition to liver disease, pathologies of the duodenum are associated with hepatic fibrosis. Changes in duodenal histopathology such as edema; increased cellular infiltration; irregularly-distributed microvilli and distorted microvilli; polyposis; vascular ectasia, congestion and/or thrombi; smooth muscle proliferation, mucosal resurfacing and fibrosis have been observed, and these conditions may also ameliorated with reversal of hepatic fibrosis. Thus, in some embodiments, the therapeutically effective amount of the pharmaceutical composition of the invention, such as OM-ZMS, may be one that which is sufficient to reduce or improve at least one pathophysiological symptom in the duodenum that is associated with hepatic fibrosis, such as edema, vascular congestion, increased cellular infiltration, and irregularly-distributed and distorted microvilli.

In yet another embodiment, the subject is a rat that has been chemically treated with a substance, such as thioacetamide (TAA) to induce hepatic fibrogenesis as a model of chronic hepatic fibrosis in humans. Carbon tetrachloride ($CCl_4$) is known as an agent for chemical induction of hepatic fibrosis. Unlike $CCl_4$, TAA toxicity does not depend only on induction of oxidative stress, but other mechanisms are also involved. Thus, the TAA-hepatotoxic model simulates clinical situations where multiple precipitating factors and different mechanisms are contributing to development and progression of liver fibrosis. Furthermore, the TAA-induced model provides a prolonged injury and recovery profile that is suitable for studying mechanisms of fibrogenesis. The substance is administered to the rat in a sufficient amount and for a suitable time period to promote fibrogenesis until reaching full fibrosis. A period of administration is preferred to be for at least 8 weeks to allow full development of fibrosis. When allowed to develop fully, the fibrosis is treated with ZMS encapsulating a drug, as exemplified herein with a therapeutically effective amount of OM-ZMS. Thus, the rat model of "already-established" chronic hepatic fibrosis is useful for studying the effects of hepatic fibrosis, such as morphological changes in the duodenum associated with hepatic fibrosis. The rat model of "already-established" chronic hepatic fibrosis is also useful for identifying agents for new treatments and assaying responses to the new treatments.

OM is a highly lipophilic ARB with antihypertensive, anti-inflammatory, and other cardiovascular beneficial effects. The oral bioavailability of olmesartan is very low (4.5%), and even its preparation as a prodrug through esterification with the medoxomil moiety just increased it to 28.6% due to its hydrophobic nature, low water solubility, and efflux by drug resistance pumps in the GIT (Kobayashi et al. 2000; *Analyt Biochem* 287(2):272-27). After oral intake, OM is rapidly cleaved by esterases in the gut mucosa, portal blood, and liver to release olmesartan, the active form, before it comes into systemic circulation. Following IV administration, olmesartan has a relatively low volume of distribution (Vd) of about 15-25 L indicating that it is mainly distributed in the extracellular compartment which may be due to its extensive protein binding. However, the Vd was higher (34.9 L) after oral administration of OM at a dose of 20 mg. Also, OM was safe and well tolerated at doses of up to 160 mg/day The plasma concentration of olmesartan approached a steady state after 5 days of treatment with OM and administration of OM once daily for 10 days did not result in drug accumulation (Schwocho et al. 2001; *J Clin Pharmacol* 41(5):515-527). OM is a competitive and selective AT1 receptor blocker with almost no antagonistic effects on the AT2 and AT4 receptors. Also, it has an inverse agonist activity due to its unique structure having a hydroxyl group at the imidazole ring and a carboxyl group. In addition, it upregulates ACE2, stimulates the tissue-protective ACE2/Ang-(1-7)/Mass receptor pathway, inhibits ACE, and decreases plasma level of angiotensin II. It binds tightly to AT1 receptor showing a high degree of insurmountability and slow dissociation. AT1 receptors are either constitutively active or activated by mechanical stretching of cells without involvement of AT II. This stretch-induced AT II-independent activation of the AT1 receptor blocker is inhibited by inverse agonists because the multivalent drug-receptor interactions between the inverse agonist and the AT1 receptor cooperate to keep the receptor in an inactive configuration in response to the different processes that results in an AT II-independent activation of the AT1 receptor (Qin et al. 2009; *Hyperten Res* 32(10):875)

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary designs and methods for fabricating and using microgrippers of the invention. These Examples describe materials and methods for using embodiments illustrated in FIGS. 1-12. Additional details can be found in the section entitled "Brief Description of the Drawings".

Example 1. Zeinmersomes

A diagram of the general structure of a ZMS is shown in FIG. 1. A solution of phospholipids (Phospholipon 90G, or PL), zein, and PEG-polymers (PEG-PLGA) can be mixed under specific conditions and permitted to self-assemble into a vesicle such as the one shown in FIG. 1. The zeinmersome vesicle of FIG. 1 is bounded by a thin membrane comprising two layers of the phospholipid PL. The PL are amphiphilic molecules, having a hydrophilic phosphate head and a hydrophobic tail consisting of two fatty acid chains. Thus, the vesicle comprises a hydrophilic core area surrounded by the inward face of the bilayer membrane. The PEG-PLGA spans the bilayer and is oriented in either an outward or an inward orientation with regards to a hydrophilic polymer "tail". The tail is typically oriented in the direction that is energetically favorable, i.e., the direction that requires the least amount of energy to maintain. Small ovals in the diagram in FIG. 1 represent molecules of a hydrophobic drug, which intercalates within or is encapsulated by the hydrophobic lipid region partitioned between the PL bilayers. Small circles represent molecules of a hydrophilic drug, which preferentially is "trapped" or encapsulated in the central hydrophilic core region. In some embodiments, the zeinmersome may comprise more than one drug within the same or different partitions, while other embodiments may comprise only one drug within a single partition.

Example 2. Formulation of ZMS Encapsulating a Drug

Preparation of OM-ZMS

In this example, OM is the only drug encapsulated in the ZMS, thus forming OM-ZMS. Because OM is a hydrophobic molecule, it is represented by the small ovals intercalated in the bilayer region in FIG. 1. The OM was a kind gift from Jamjoom Pharmaceuticals Co. (Industrial Area, Jeddah, KSA). Poly (ethylene glycol) methyl ether-block-poly (lactide-co-glycolide) (PEG-PLGA) PEG Mn 2,000, PLGA Mn 4,500, zein and ethanol were purchased from Sigma Aldrich Co (St. Louis, Mo., US). Phospholipon 90 G (PL) was purchased from American Lecithin Co (Oxford, Conn., US). OM (0.1% w/v) and PL (0.5% w/v) were dissolved in ethanol under stirring using a magnetic stirrer. Zein (0.1% w/v) and PEG-PLGA copolymer (0.2% w/v) were dissolved in 85% ethanol stirred using a magnetic stirrer. Both solutions were mixed under stirring. After that, the ethanolic solution was evaporated in a Rotavapor® R-200 (Buchi, Germany). The formed layer was kept in a vacuum cabinet (Thermo Scientific, Model 5831) overnight. Deionized water was added to the deposited layer. The mixture was rotated at 100 rpm for 1 h at 45° C. The obtained vesicles were maintained at the same temperature for 1 h to allow swelling. The resulting vesicles were ultrasonicated for 8 min per cycle for 2 cycles utilizing a Sonics Vibra-Cell™ tapered microtip of amplitude 40%, 750 W, 20 kHz (Sonics & Materials Inc., CT, US) in an ice bath to yield vesicles in the nanosize range. The vesicles of the final product were analyzed as described in Example 3 and/or were lyophilized and stored under nitrogen until further use.

Example 3. Characterization of OM-ZMS Nanoparticles

Determination of OM Encapsulation Efficiency

OM was encapsulated in OM-ZMS as described in Example 2. The prepared OM-ZMS NPs showed EE % of 95.73±3.28%. Drug encapsulation efficiency (EE %) was determined by equation (1).

$$\text{OLME EE \%} = \text{Mass of drug in nanostructures/Mass of feed drug} \times 100 \quad \text{equation (1)}$$

Particle Size and Zeta Potential Analysis

Figure 2A:
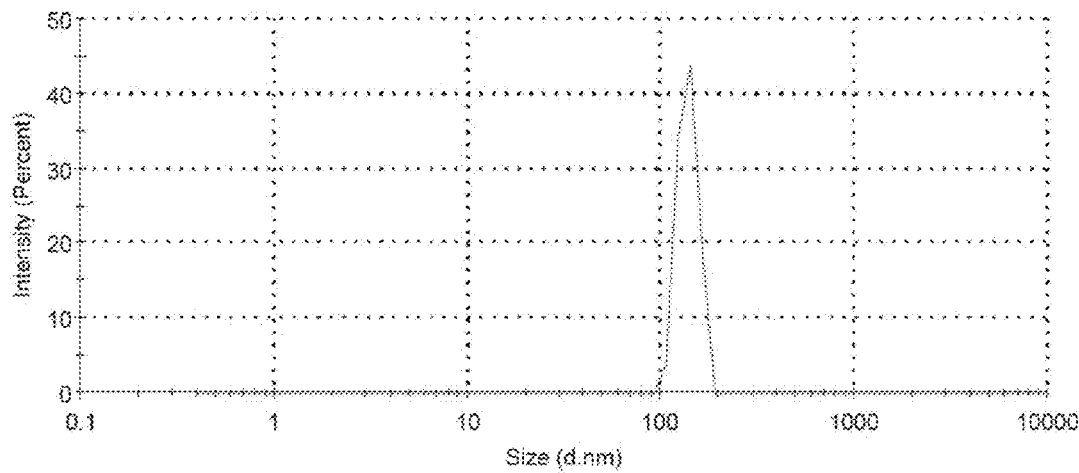
FIGS. 2A and 2B show analyses of the prepared OM-ZMS nanoparticles.
Figure 2B:
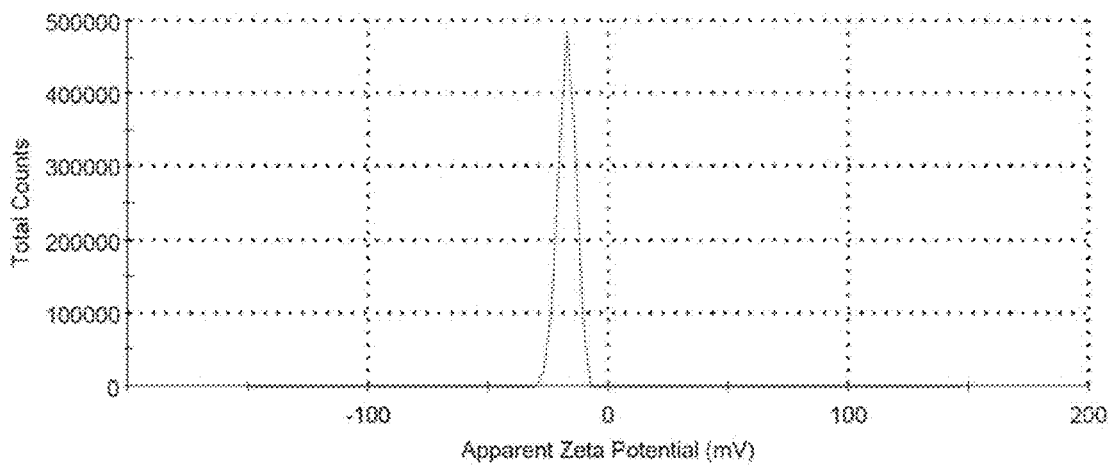
Figure 3:
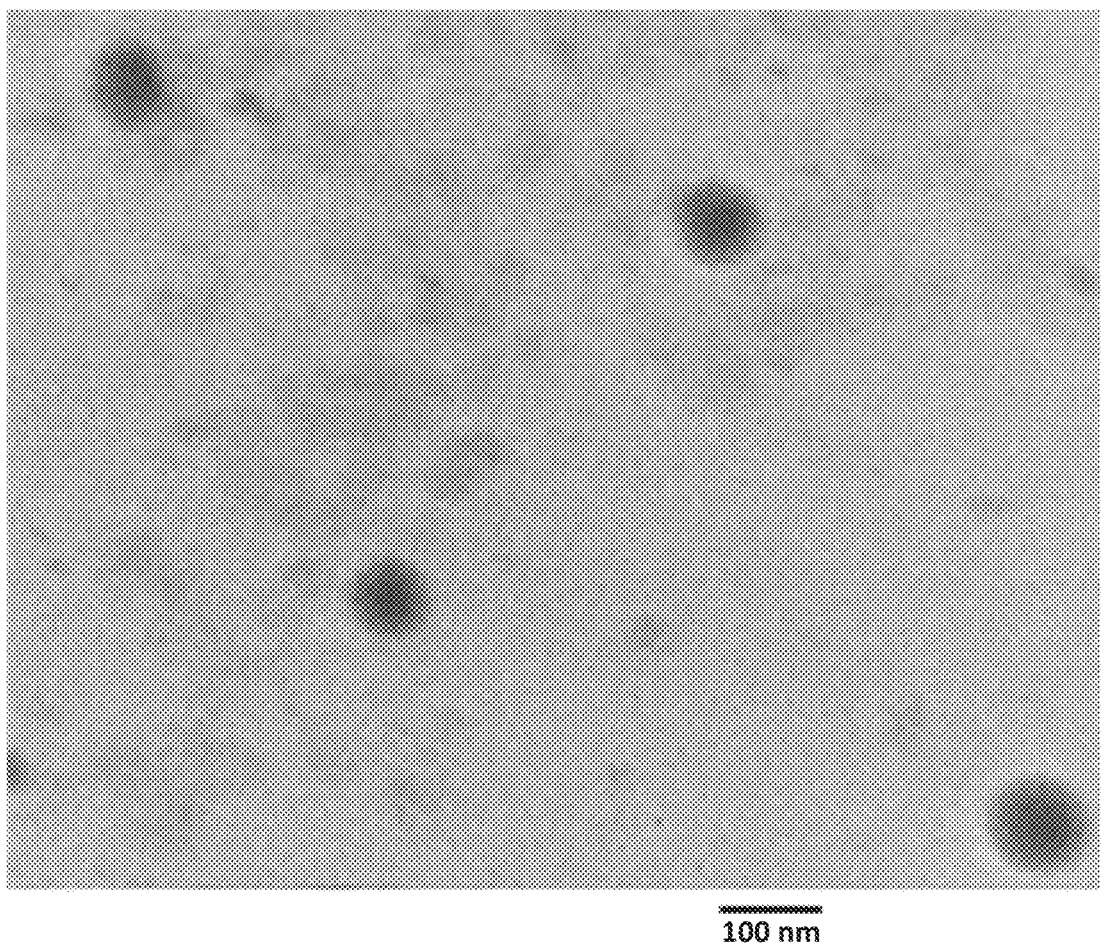
FIG. 3 is an image obtained using transmission electron microscopy showing the relative size and shape of the OM-ZMS nanoparticles. Magnification bar is 100 nm.

The prepared OM-ZMS were analyzed for particle size and zeta potential using Malvern ZSP (Malvern Panalytical Ltd, Enigma Business Park, Malvern, United Kingdom). A sample taken from prepared OM-ZMS was dissolved in ethanol and passed through a 0.22-μm filter prior to being subjected to a high-performance liquid chromatography (HPLC) protocol. The formulations were diluted twenty times. The average of particle size and zeta potential were expressed using three replicate samples. The average size of the particles was 137.8±6.4 nm, as shown in FIG. 2A, and the zeta potential was −17.5±3.61 mV, as shown in FIG. 2B.

Transmission Electron Microscope Investigation

The prepared OM-ZMS were observed under a transmission electron microscope (TEM) (JEM-2100, Japan Electronics Corporation) to determine relative size and shape of the nanoparticles. Samples were diluted 10-fold with distilled water, and a small amount of solution was dropped on the copper screen for volatilization and drying. A drop of 3% phosphotungstic acid solution was used for negative staining. After drying for 20 min., nanoparticles were put under the TEM for observation. Sizes of the analyzed nanoparticles were determined using a relative size measurement by Malvern ZSP (Malvern Panalytical Ltd; Malvern, UK). The OM-ZMS showed spherical nanostructures, with a smooth surface with a size in the range of 95 nm to 200 nm, with an average size of approximately 137.8±6.4 nm, as indicated by the representative TEM image shown in FIG. 3.

In Vitro Diffusion Studies

The formula characterization was assessed by examining its diffusion pattern. An automated Franz diffusion cell apparatus (MicroettePlus; Hanson Research, Chatsworth, Calif., US) with a diffusion area of 1.76 cm$^2$ was utilized to examine the diffusion of OM from the prepared formula as described previously (Ahmed et al., 2019. Internat J Pharmaceu 570: 118657). A 0.1 μm nylon diffusion membrane and a buffer (pH 7.0) containing Tween 20 (0.5% w/v) were used, and this was stirred at 400 rpm. The aliquots were analyzed for OM concentration by HPLC as previously reported. The samples were collected at 0.5, 1, 2, 4, 8, 12, 24 and 48 h.

Figure 4:
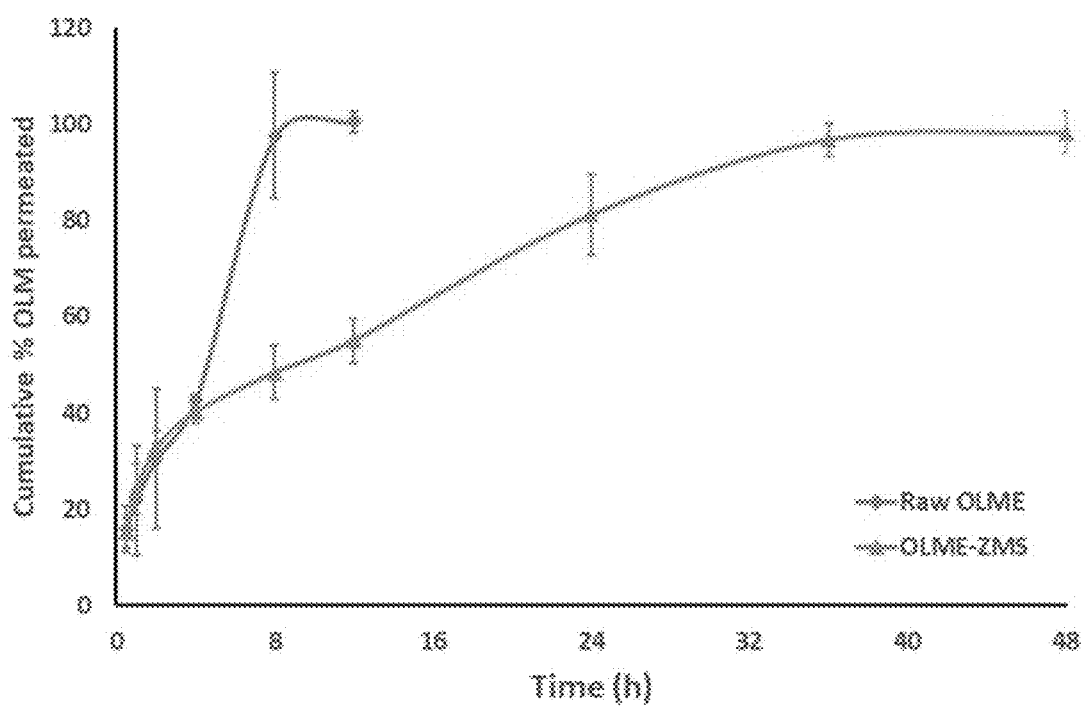
FIG. 4 shows the in vitro diffusion rate of OM from OM-ZMS (OLME-ZMS) compared to raw OM (Raw OLME) over a 48-hour period.
Figure 5A:
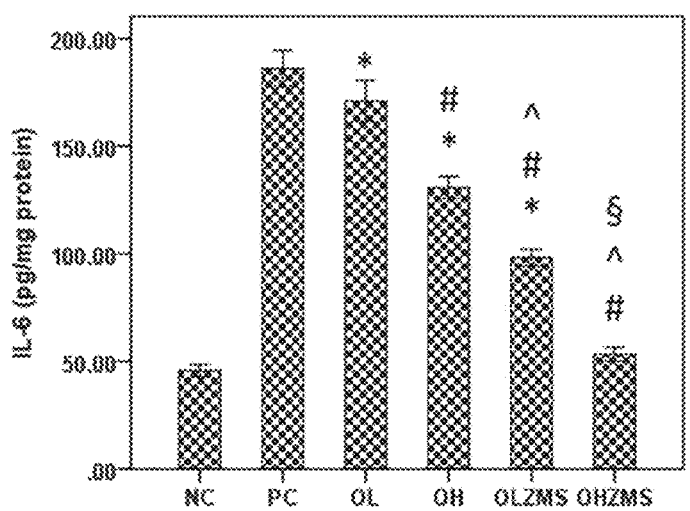
FIGS. 5A and 5B show the effects of the free or raw drug OM in a low dose (OL) or a high dose (OH), as compared to the effects of OM-ZMS formulations in a low dose (OLZMS) or a high dose (OHZMS), as assayed by measuring the concentrations of IL-6 (5A) and TNF-α (5B) in liver homogenate in TAA-induced hepatic fibrosis rats (n=8). Data are expressed as mean±SEM. *: $P<0.05$ vs. Normal control (NC), #: $P<0.05$ vs. Positive control (PC) and OL, ^: $P<0.05$ vs. OH, §: $P<0.05$ vs. OLZMS
Figure 5B:
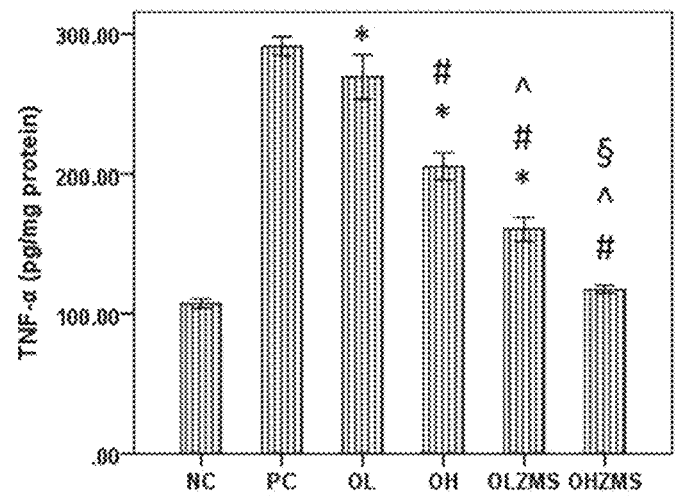
Figure 6A:
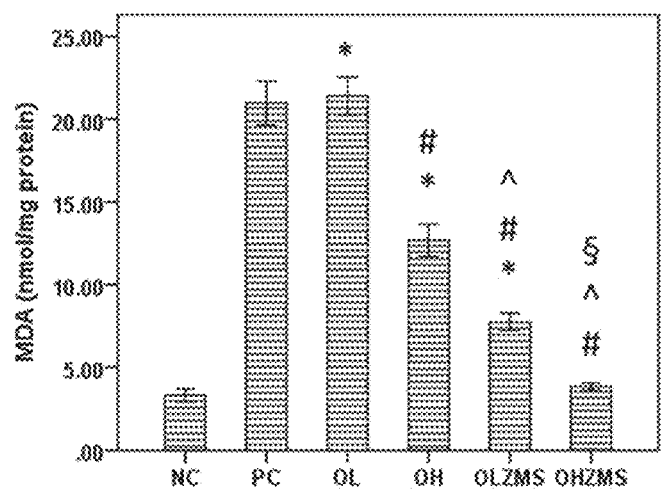
FIGS. 6A and 6B show effects of OL, OH, OLZMS and OHZMS on concentrations of MDA (6A) and GSH (6B) in liver homogenate in TAA-induced hepatic fibrosis rats (n=8). Data are expressed as mean±SEM. *: $P<0.05$ vs. Normal control (NC), #: $P<0.05$ vs. Positive control (PC) and OL, ^:$P<0.05$ vs. OH, §: $P<0.05$ vs. OLZMS
Figure 6B:
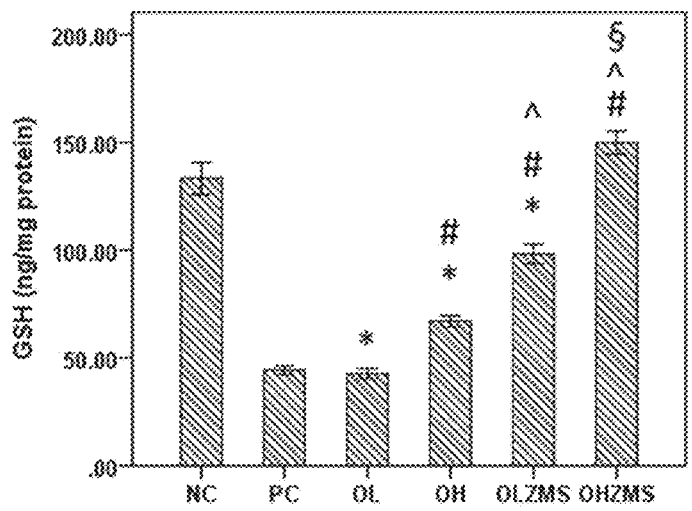

FIG. 4 shows the percentage of free OM that permeated from and aliquot of prepared OM-ZMS NPs formula, compared with and aliquot of raw OM. The raw OM demonstrated a diffusion of almost 97.5±13.07% within a 4-hour time period. The OM-ZMS NPs demonstrated controlled a permeation pattern over a 48-hour time period, reaching a final value of 98.21±4.46% by the end of the 48 hours.

Example 4. A Method of Providing a Model of Human Chronic Hepatic Fibrosis for Testing ZMS-Based Therapeutics.

The protocol for this study was approved by the King Abdulaziz University Research Ethics Committee and adhered to the international guidelines for the Care and Use of Laboratory Animals. Adult Sprague-Dawley male rats weighing 200-250 g were obtained from King Fahd Research Center and housed in cages at 20-22° C. room temperature in a 12 h light-dark cycle. After one week of acclimatization, rats were used in the experiment. Food and water were available ad libitum.

Induction of liver fibrosis by TAA occurs due to its very reactive metabolite (TAA sulphur dioxide, TAA-s-s-dioxide) which results from its oxidation by CYP2E1 enzymes in the microsomes of the hepatic cells (Kim et al. 2000; *Toxicol Letters* 114(1-3):225-235). It interferes with movement of RNA from nucleus to cytoplasm resulting in membrane injury and alteration in cell permeability. Also, it increases concentration of the intracellular calcium, karyomegaly with increased nuclear volume, and mitochondrial inhibition which ultimately results in hepatic cell death. TAA-induced liver injury has a prolonged injury and recovery profile allowing enough time to study mechanisms. TAA leads to varying degrees of hepatotoxicity including necrosis of parenchyma cells, nodular cirrhosis, and proliferation of hepatic cells. Unlike $CCl_4$, TAA toxicity does not depend only on induction of oxidative stress but other mechanisms are also involved. Thus, TAA-hepatotoxic model simulates some clinical situations where multiple precipitating factors and different mechanisms share in development and progression of liver fibrosis (Yanguas et al. 2016; *Arch Toxicol* 90(5): 1025-1048).

Rats were given freshly prepared TAA (0.9% w/v in saline solution, 200 mg/kg, ip) twice weekly for eight weeks. A normal control (NC) group of rats (n=8) received injections of the vehicle twice weekly for eight weeks. The TAA-treated rats were randomly assigned to groups (n=8), including a test group for each dosage of a free drug (not encapsulated in ZMS), each dosage of zeinmersomes encapsulating the drug, and a positive control group (PC) having hepatic fibrosis but receiving a vehicle-only treatment instead of a drug treatment.

Example 5. A Method of Administering OM or OM-ZMS

Five groups of rats (n=8) were given freshly prepared TAA (0.9% w/v in saline solution, 200 mg/kg, ip) twice weekly for eight weeks and a normal control (NC) group received vehicle injections, as described in Example 4. The five TAA groups included a positive control group (PC, untreated) and four groups treated with low and high doses (2 and 4 mg/kg/day) of OM as raw drug (OL & OH, respectively) and the same low and high doses (2 and 4 mg/kg/day) of OM formulated as zeinmersomes (OLZMS & OHZMS, respectively). The OM standard drug was suspended in distilled water containing 0.25% w/v carboxymethyl cellulose. The doses were given by oral gavage once daily for two months. In other experiments, the doses ranged from 1 mg/kg/day to 16 mg/kg/day (data not shown).

At the end of treatment duration, blood samples were withdrawn from the retro-orbital plexus of the rats under light ether anesthesia. Plasma was separated and kept at −80° C. until analysis. Then, the rats were sacrificed by cervical dislocation under ether anesthesia. Liver and duodenum were isolated and parts of each were kept in 10% formalin-saline for histopathological examination. Other portions of liver tissue were homogenized. The plasma levels of ALT and AST and the homogenate levels of IL-6, reduced glutathione (GSH), TNF-α, malondialdehyde (MDA), and protein content were measured using ELISA kits (MyBioSource, Inc. CA, USA). In addition, the concentrations of olmesartan in plasma and liver homogenate were measured by HPLC/MS.

Data are expressed as mean±SEM Comparisons between different groups were carried out using one-way analysis of variance (ANOVA) followed by Bonferroni test for multiple comparisons. The SPSS software, version 22 (US) was used to carry out these statistical tests. The difference was considered significant when $P<0.05$.

Assessment of Liver Function in Response to OM-ZMS

The levels of ALT and AST were measured by using ELISA commercially available kits according to the manufacturer's protocol. The TAA-induced fibrotic rats showed significant increases of the plasma levels of ALT and AST. All treatments except for OL significantly reversed these TAA-induced changes. The OLZMS and OHZMS groups showed significant differences from the OH group while the OHZMS group showed a significant difference from the OLZMS group. The OHZMS group showed a non-significant difference from the NC group. These results are summarized in Table 1.

TABLE 1

Effects of low and high doses of OM, formulated at as raw drug (OL, OH) or as ZMS-encapsulated OM (OLZMS, OHZMS), on plasma concentrations of ALT and AST in TAA-induced hepatic fibrosis rats (n = 8).

|  | NC | PC | OL | OH | OLZMS | OHZMS |
|---|---|---|---|---|---|---|
| ALT (U/L) | 31.45 ± 0.92 | 120.13 ± 1.63 | 114.88 ± 1.23* | 81.41 ± 1.30*,# | 70.13 ± 5.38*,#,^ | 27.33 ± 1.05#,^,§ |
| AST (U/L) | 47.98 ± 1.59 | 211.75 ± 6.25 | 198.32 ± 6.46* | 169.00 ± 2.32*,# | 133.33 ± 7.41*,#,^ | 44.59 ± 2.29#,^,§ |

Data are expressed as mean ± SEM.
*P < 0.05 vs. Normal control (NC),
P < 0.05 vs. Positive control (PC) and OL,
^P < 0.05 vs. OH,
§P < 0.05 vs. OLZMS.

Inflammatory and Oxidative Markers in Response to OM-ZMS

A part of the liver of each animal was rapidly dissected out, washed, and homogenized in phosphate-buffered saline (0.01M PBS, pH 7.4) using a TissueLyser II (Qiagen; Venlo, Netherlands) at 4° C. to produce a 10% homogenate. The homogenates were centrifuged at 10000 rpm for 15 min at 4° C. and the supernatant was kept at −80° C. till time of analysis. The levels of TNF-α, IL-6, malondialdehyde (MDA), and reduced glutathione (GSH) were measured by the ELISA kits using a micro plate reader (Versa Max, Molecular Devices). The protein content in the liver homogenate was determined by using a colorimetric kit based on Bradford method (Bradford 1976) and the levels of IL-6, TNF-α, GSH, and MDA were expressed/mg protein.

The IL-6 level was measured by using the competitive enzyme immunoassay technique utilizing a polyclonal anti-IL-6 antibody and an IL-6-HRP conjugate. The assay sample and buffer were incubated together with IL-6-HRP conjugate in pre-coated plate for one hour. After washing, the wells were then incubated with a substrate for HRP enzyme. The product of the enzyme-substrate reaction formed a blue colored complex. Finally, a stop solution was added to stop the reaction, which then turned the solution yellow. Absorbance was read at 450 nm in a microplate reader.

The TNF-α level was measured by using the principle of double antibody sandwich ELISA technique is used. Anti-TNF-α antibody was pre-coated on the wells. Add biotin labeled anti-TNF-α antibodies to combine with the antigens on immune complexes. Avidin-Biotin-Peroxidase Complex was added, and unbound conjugates were washed away with wash buffer. TMB substrates were used to visualize HRP enzymatic reaction producing a blue color product that changed into yellow after adding acidic stop solution. The density of yellow is proportional to TNF-α amount of sample captured in plate. Absorbance was read at 450 nm.

The GSH level was measured by using the principle of double antibody sandwich ELISA technique. Anti-GSH antibody was pre-coated on the wells. Add biotin labeled anti-GSH antibodies to combine with the antigens on immune complexes. Horseradish peroxidase was added to label the avidins and incorporate them with the biotin labeling antibodies. Substrates were added for coloring and the concentrations of specimens were calculated.

The MDA level was measured by using the competitive enzyme immunoassay technique utilizing a polyclonal anti-MDA antibody and an MDA-HRP conjugate. The assay sample and buffer were incubated together with MDA-HRP conjugate in pre-coated plate for one hour. After washing, the wells were then incubated with a substrate for HRP enzyme. The product of the enzyme-substrate reaction formed a blue colored complex. Finally, a stop solution was added to stop the reaction, which then turned the solution yellow. Absorbance was read at 450 nm in a microplate reader.

The PC rats showed significant increases of the levels of IL-6 compared to NC rats (shown in FIG. 5A), TNF-α (shown in FIG. 5B), and MDA (shown in FIG. 6A) and a significant decrease of GSH level (shown in FIG. 6B) in the liver homogenate. All treatments except for OL significantly reversed these TAA-induced changes. The OLZMS and OHZMS groups showed significant differences from the OH group while the OHZMS group showed a significant difference from the OLZMS group. The OHZMS group showed a non-significant difference from the NC group.

Histopathology of Hepatic and Duodenal Sections Following Administration of OM-ZMS Samples of the liver were fixed in 10% phosphate-buffered formalin and then embedded in paraffin. Sections of 3-5 μm thickness were cut, stained with H&E, examined for estimation of fibrosis, inflammatory cell infiltration, and hepatocytic degeneration, and the lesions were reported as mild, moderate or severe, as in Ramadan et al. (Chemico-Biologic Interact. 2018; 289: 109-118).

Figures 7A, 7B, 7C, 7D, 7E, 7F:
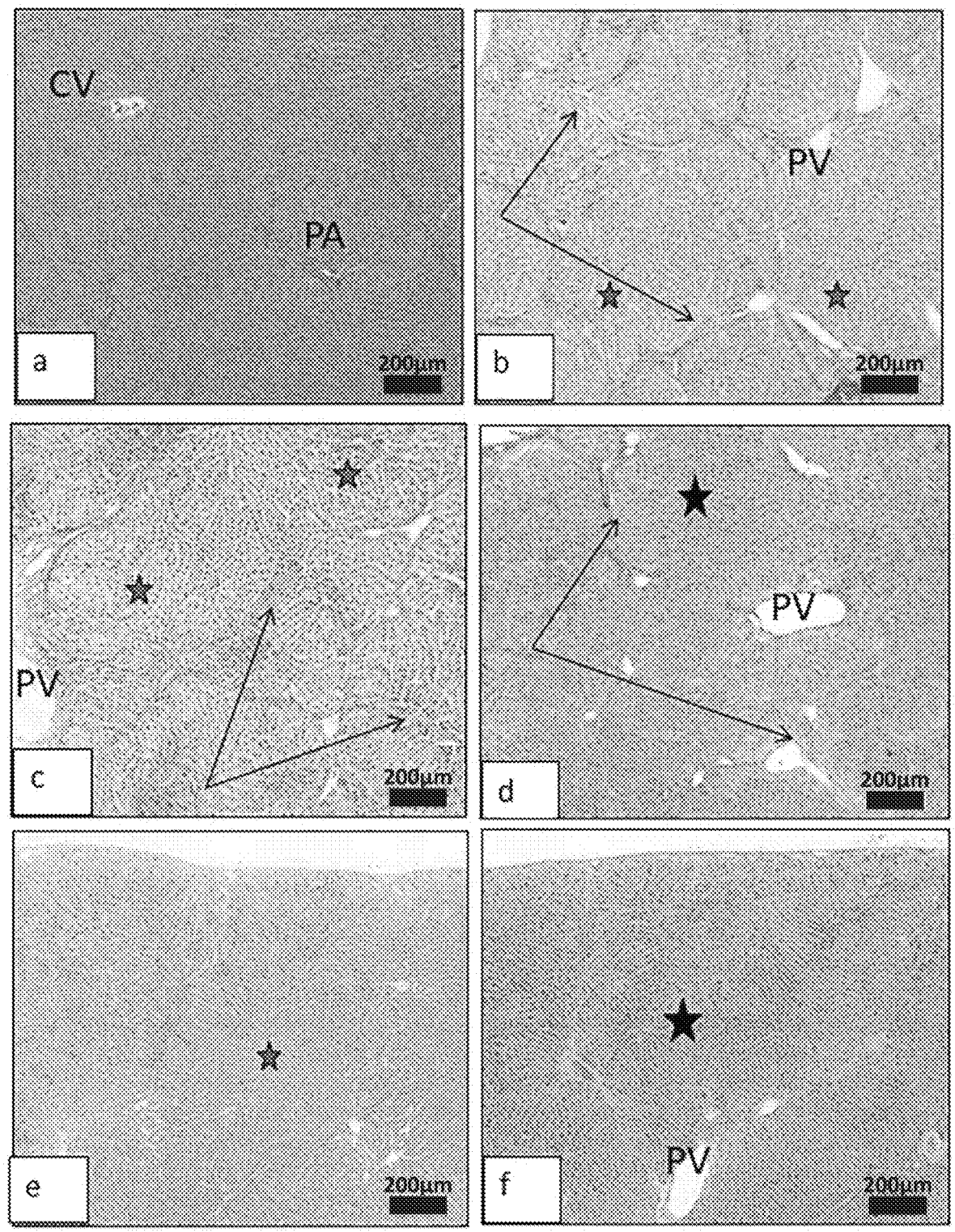
FIGS. 7a-7f show low power (X10) microphotographs of liver sections of: (a) normal control rats showing ill-defined hepatic lobulation between the central vein (CV) and the portal area (PA) regions and normal hepatocytes. (b) thioacetamide (positive control) rats showing definitive hepatic lobulation (arrows) due to proliferation of fibroblasts bridging between central vein and the portal vein (PV). There are marked inflammatory infiltration (stars) and perivascular fibrosis with congestion of the blood vessels. (c) OL-treated rats showing no improvement while (d) OH-treated rats showing some improvement with mild decrease of hepatic lobulation (arrows) and inflammatory infiltrates (stars). (e) OLZMS-treated rats and (f) OHZMS-treated rats showing dose-dependent protection with ill-defined hepatic lobulation, decreased intensity of fibrous proliferation, and minimal inflammatory infiltrate (stars). The OHZMS group shows a nearly-normal picture with normal appearance of the hepatic parenchymal cells. The histological findings in these images were analyzed in comparison with the histological findings of images shown at high magnification in FIGS. 8A-8F.

The NC rats showed ill-defined normal hepatic lobulation with normal appearance of hepatocytes. The PC rats showed definitive hepatic lobulation due to proliferation of fibroblasts, marked inflammatory infiltration, and congestion of the blood vessels. Hepatocytes were swollen with degenerative changes. All treatments except for OL reversed these TAA-induced changes with varying degrees, as compared to the fibrotic PC rats. The OH-treated rats showed mild improvement with persistence of hepatic lobulation, inflammatory infiltrate, and degenerative changes in hepatocytes. The OLZMS and OHZMS groups showed good protection with ill-defined hepatic lobulation, minimal inflammatory infiltrate, and minimal residual hepatocytes degenerative changes. The protection was even more pronounced in the OHZMS group with a nearly normal appearance of the hepatocytes, as shown in FIGS. 7a-7f and FIGS. 8A-8F. Each figure shows a representative image acquired from a tissue section, with FIGS. 7a-7f showing low power magnification (X10) microphotographs of liver sections of rats and FIGS. 8A-8F showing high power magnification (X60) microphotographs of liver sections of rats as follows:

FIGS. 7a and 7b show images of a liver section from (a) normal control rat showing ill-defined hepatic lobulation between the central vein (CV) and the portal area (PA) regions and normal hepatocytes and a liver section from (b) thioacetamide (positive control) rat showing definitive hepatic lobulation (arrows) due to proliferation of fibroblasts bridging between central vein and the portal vein (PV). There are marked inflammatory infiltration (stars) and perivascular fibrosis with congestion of the blood vessels.

FIGS. 7c and 7d show images of a liver section from (c) OL rat showing no improvement and a liver section from (d) OH rat showing some improvement with mild decrease of hepatic lobulation (arrows) and inflammatory infiltrates (stars).

FIGS. 7e and 7f show images of a liver section from (e) OLZMS rat and a liver section from (f) OHZMS rat showing dose-dependent protection with ill-defined hepatic lobulation, decreased intensity of fibrous proliferation, and minimal inflammatory infiltrate (stars). The OHZMS group shows a nearly-normal picture with normal appearance of the hepatic parenchymal cells.

Figures 8A, 8B, 8C, 8D, 8E, 8F:
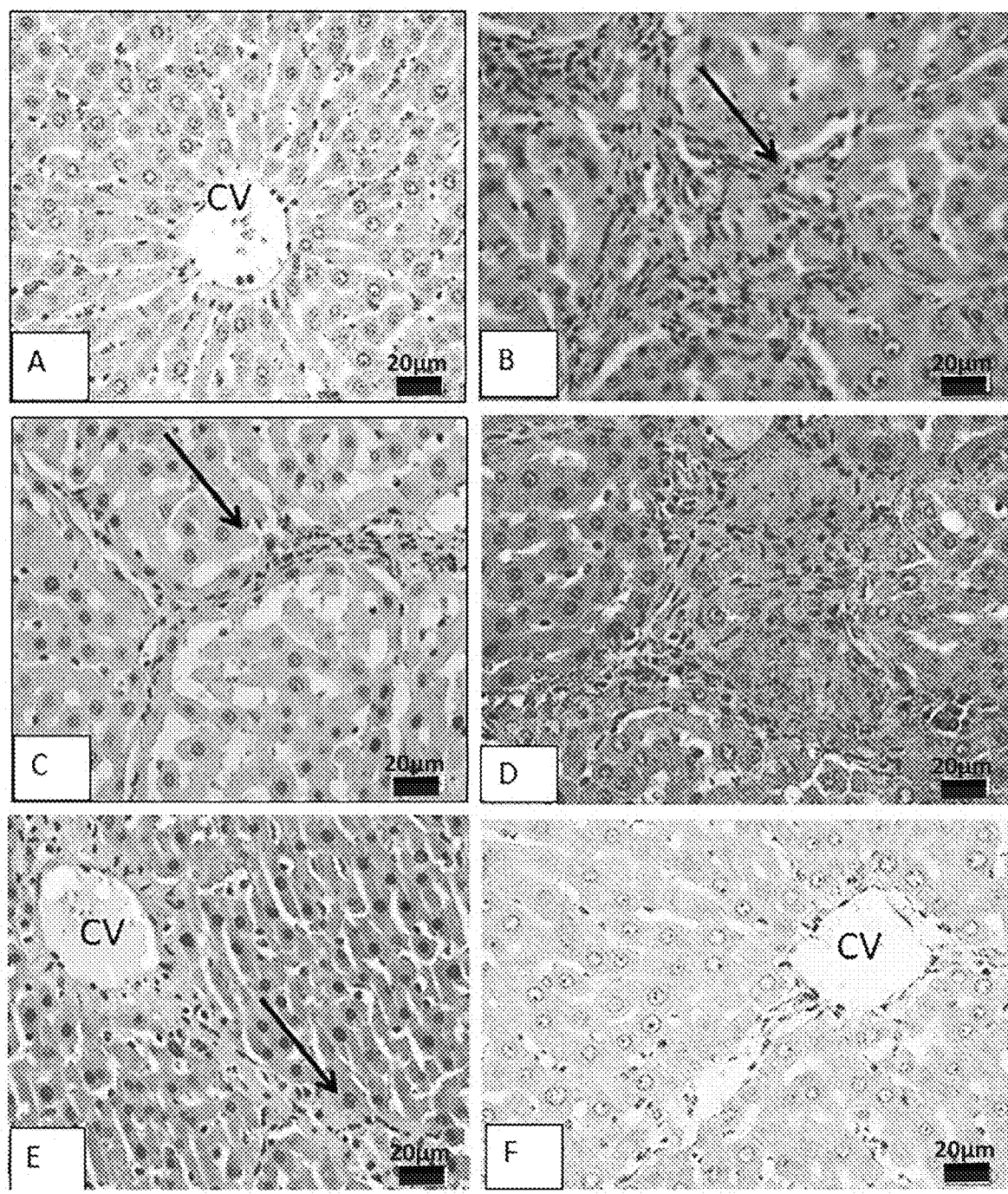
FIGS. 8A-8F show high power (X60) microphotographs of liver sections of: (A) normal control rats showing ill-defined hepatic lobulation between the central vein (CV) and the portal area (PA) regions and normal hepatocytes. (B) thioacetamide (positive control) rats showing definitive hepatic lobulation (arrows) due to proliferation of fibroblasts bridging between central vein and the portal vein (PV). There are marked inflammatory infiltration and perivascular fibrosis with congestion of the blood vessels. Hepatocytes are swollen with karyomegaly, degenerative, necrosed, or apoptotic and there is nuclear pyknosis. (C) OL-treated rats showing no improvement while (D) OH-treated rats showing some improvement with mild decrease of hepatic lobulation, inflammatory infiltrates, and degenerative hepatocyte changes. (E) OLZMS-treated rats and (F) OHZMS-treated rats showing dose-dependent protection with ill-defined hepatic lobulation, decreased intensity of fibrous proliferation, and minimal inflammatory infiltrate. Most hepatocytes looked normal with minimal residual degenerative changes. Nuclei of cells are dark with heterochromatin due to inactivation. The OHZMS group shows a nearly-normal picture with normal appearance of the hepatic parenchymal cells. The histological findings in these images were analyzed in comparison with the histological findings of images shown at low magnification in FIGS. 7a-7f.

FIGS. 8A and 8B show images of a liver section from (A) normal control rat showing ill-defined hepatic lobulation between the central vein (CV) and the portal area (PA) regions and normal hepatocytes and a liver section from (B) thioacetamide (positive control) rat showing definitive hepatic lobulation (arrows) due to proliferation of fibroblasts bridging between central vein and the portal vein (PV). There are marked inflammatory infiltration and perivascular fibrosis with congestion of the blood vessels. Hepatocytes are swollen with karyomegaly, degenerative, necrosed, or apoptotic and there is nuclear pyknosis.

FIGS. 8C and 8D show images of a liver section from (C) OL rat showing no improvement and a liver section from (D) OH rat showing some improvement with mild decrease of hepatic lobulation, inflammatory infiltrates, and degenerative hepatocyte changes.

FIGS. 8E and 8F show images of a liver section from (E) OLZMS rat and a liver section from (F) OHZMS rat showing dose-dependent protection with ill-defined hepatic lobulation, decreased intensity of fibrous proliferation, and minimal inflammatory infiltrate. Most hepatocytes looked normal with minimal residual degenerative changes. Nuclei of cells are dark with heterochromatin due to inactivation. The OHZMS group shows a nearly-normal picture with normal appearance of the hepatic parenchymal cells.

Figures 9A, 9B, 9C, 9D, 9E, 9F:
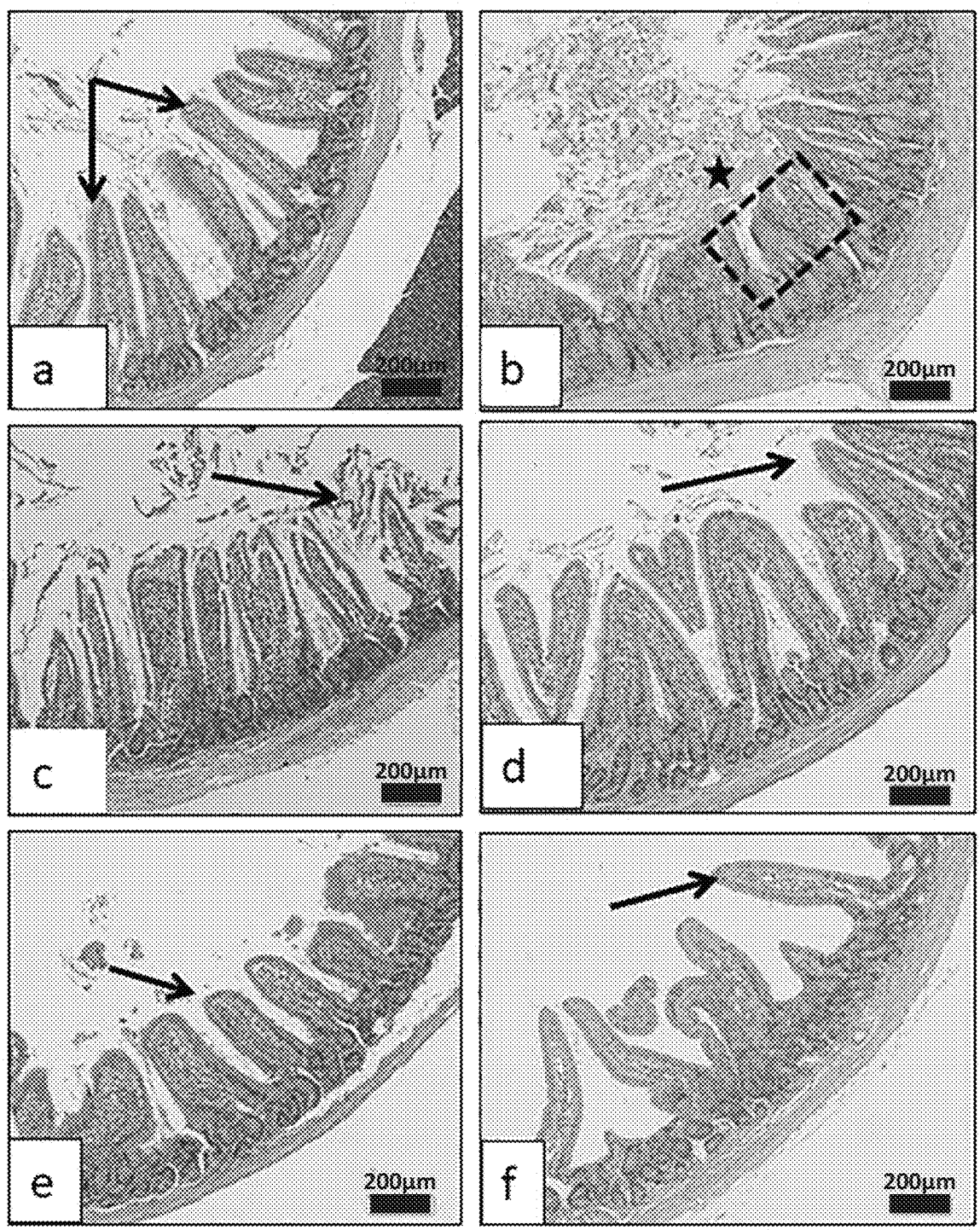
FIGS. 9a-9f show low power (X10) microphotographs of duodenal sections of: (a) normal control rats showing normal duodenal mucosa with leaf-like villi, intact surface epithelium (arrows), and normal cellular core. (b) thioacetamide (positive control) rats showing distorted villi with denuded surface epithelium, mucous in lumen (star), fused hyalinized villi (dotted square), edema, and vascular congestion. (c) OL-treated rats showing swollen distorted villi with damaged desquamated surface epithelium (arrows) and highly cellular core. (d) OH-treated rats showing some normal villi (arrows) and highly cellular core. (e) OLZMS-treated rats showing intact villus surface epithelium (arrows) with some swollen cellular core. (f) OHZMS-treated rats showing nearly-normal villi, intact surface epithelium (arrows), and thin core with normal cellular density. The histological findings in these images were analyzed in comparison with the histological findings of images shown at high magnification in FIGS. 10A-10F FIGS. 10A-10F show high power (X20) microphotographs of duodenal sections of: (A) normal control rats showing normal duodenal mucosa with leaf-like villi, intact surface epithelium (arrows), and normal cellular core. (B) thioacetamide (positive control) rats showing distorted villi with denuded surface epithelium (arrows), mucous in lumen (star), fused hyalinized villi (dotted square), edema, and vascular congestion. (C) OL-treated rats showing swollen distorted villi with damaged desquamated surface epithelium (arrows) and highly cellular core (star). (D) OH-treated rats showing some normal villi (arrows) and highly cellular core (star). (E) OLZMS treated rats showing intact villus surface epithelium (arrows) with some swollen cellular core (star). (F) OHZMS-treated rats showing nearly-normal villi, intact surface epithelium (arrows), and thin core with normal cellular density (star). The histological findings in these images were analyzed in comparison with the histological findings of images shown at low magnification in FIGS. 9a-9f.

Duodenal sections were also prepared and examined for detection of sprue-like enteropathy, if any. In general, the PC rats showed edema, vascular congestion, increased cellular infiltration, irregularly distributed and distorted villi. All treatments except for OL reversed these TAA-induced changes with varying degrees, as compared to the PC rats that received none of the OM treatments. The OH showed mild improvement. The OLZMS and OHZMS groups showed protection which was more marked with the OHZMS group with a nearly-normal appearance of the duodenum. Low and high magnification for each section is show in the representative pairs of images in FIGS. 9a-9f and 10A-10F, as follows:

FIGS. 9a and 9b are images from a duodenal section from (a) normal control rat showing normal duodenal mucosa with leaf-like villi, intact surface epithelium (arrows), and normal cellular core and a duodenal section from (b) thioacetamide (positive control) rat showing distorted villi with denuded surface epithelium, mucous in lumen (star), fused hyalinized villi (dotted square), edema, and vascular congestion.

FIGS. 9c and 9d are images from a duodenal section from (c) OL rat showing swollen distorted villi with damaged desquamated surface epithelium (arrows) and highly cellular core and a duodenal section from (d) OH rat showing some normal villi (arrows) and highly cellular core.

FIGS. 9e and 9f are images from a duodenal section of (e) OLZMS rat showing intact villus surface epithelium (arrows) with some swollen cellular core and a duodenal section from (f) OHZMS rat showing nearly normal villi, intact surface epithelium (arrows), and thin core with normal cellular density.

Figures 10A, 10B, 10C, 10D, 10E, 10F:
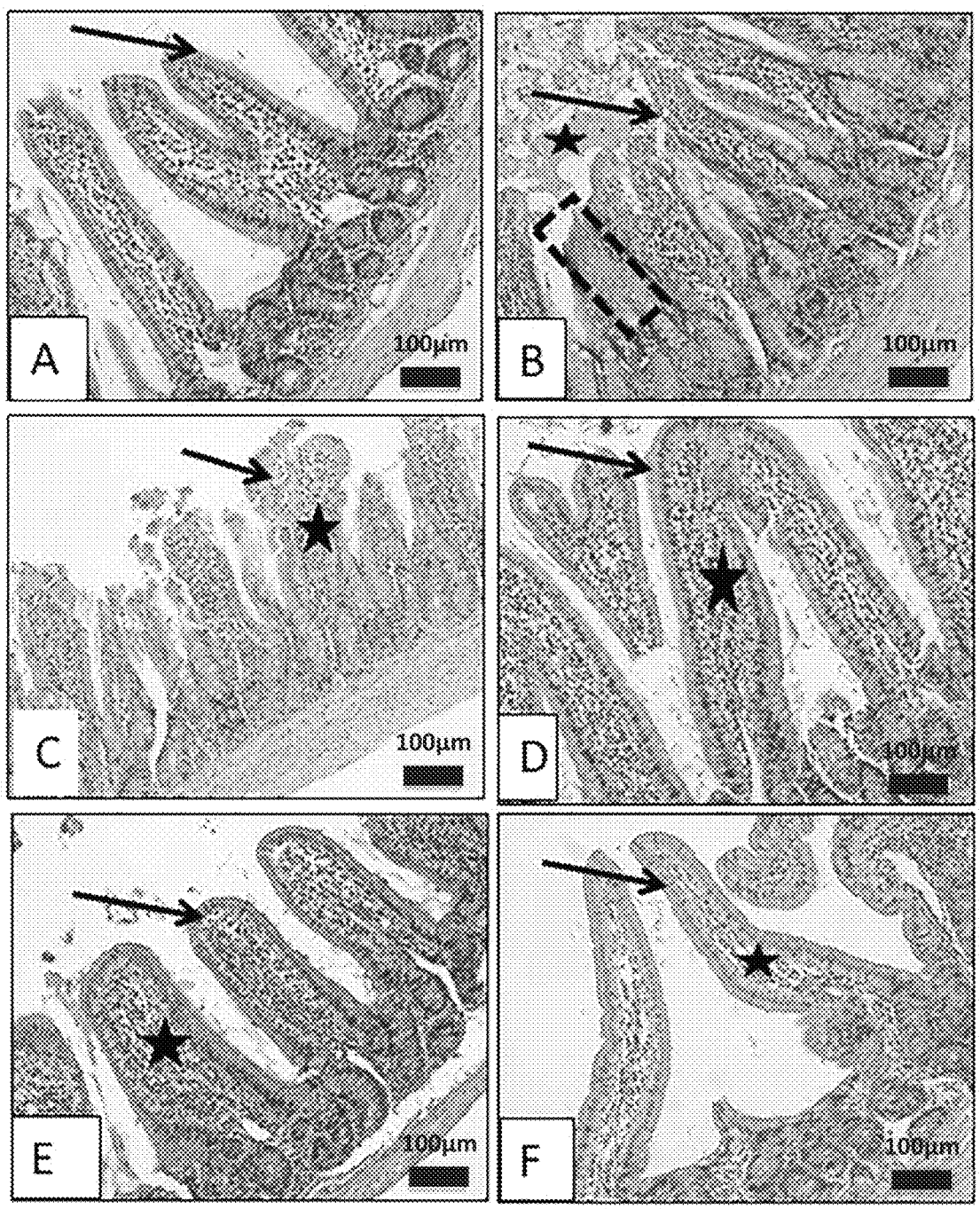

FIGS. 10A and 10B are images from a duodenal section from (A) normal control rat showing normal duodenal mucosa with leaf-like villi, intact surface epithelium (arrows), and normal cellular core and a duodenal section from (B) thioacetamide (positive control) rat showing distorted villi with denuded surface epithelium (arrows), mucous in lumen (star), fused hyalinized villi (dotted square), edema, and vascular congestion.

FIGS. 10C and 10D are images from a duodenal section from (C) OL rat showing swollen distorted villi with damaged desquamated surface epithelium (arrows) and highly cellular core (star) and a duodenal section from (D) OH rat showing some normal villi (arrows) and highly cellular core (star).

FIGS. 10E and 10F are images from a duodenal section from (E) OLZMS rat showing intact villus surface epithelium (arrows) with some swollen cellular core (star) and a duodenal section from (F) OHZMS rat showing nearly normal villi, intact surface epithelium (arrows), and thin core with normal cellular density (star).

Measurement of Free OM Concentration in Plasma and Liver.

Plasma and liver samples were obtained for measurement of olmesartan concentrations, as follows:

Liver samples were rinsed with saline, dried, and stored at −20° C. During analysis, the frozen liver samples were thawed at room temperature, weighed, and homogenized at 10 000 rpm for 5 min with ice-cold saline at a ratio 1:2 (g:ml) followed by sonication on wet ice for one min. An Agilent 6460 triple quad mass spectrometer (QqQ-MS) coupled with a diode array detector (DAD) was used for quantitative analysis (Agilent Technologies, USA).

The electrospray ionization mass spectrometer (ESI-MS) system was connected to an HPLC-Agilent 1200 system equipped with an autosampler, a quaternary pump, and a column compartment (Palo Alto, Calif., USA). The system was controlled by MassHunter software (version B.03.01, Build 3.1.346.0). The MS conditions were as follows: gas temperature, 330-C; gas flow rate, 11 L/min; nebulizer pressure; 35 psi, and capillary voltage, 4300 V. The MS settings were optimized for each compound separately, including the fragmentor voltage, dwell time, and collision energy voltage, with settings shown in Table 2.

TABLE 2

| MRM transition of OLM and InSt | | | | | |
|---|---|---|---|---|---|
| Compound Name | Precursor Ion, m/z | Product Ion, m/z | Dwell | Fragmentor, v | Collision Energy, v |
| OLM | 447.3 | 206.9 | 200 | 150 | 35 |
| InSt | 436.2 | 306.1 | 200 | 150 | 19 |

Figures 11A, 11B:
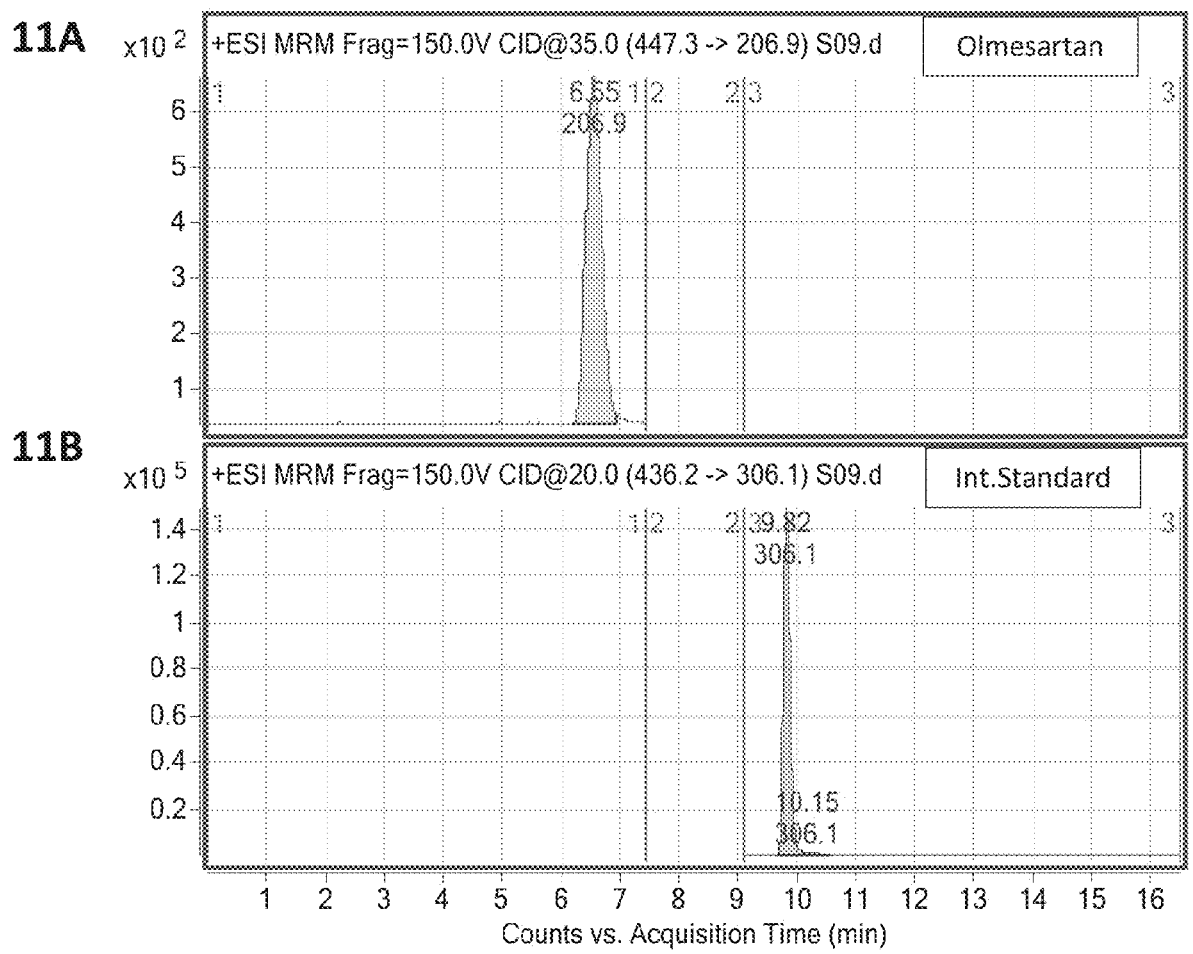
FIGS. 11A and 11B show a representative MRM transition in chromatograms of olmesartan in plasma.
Figures 12A, 12B:
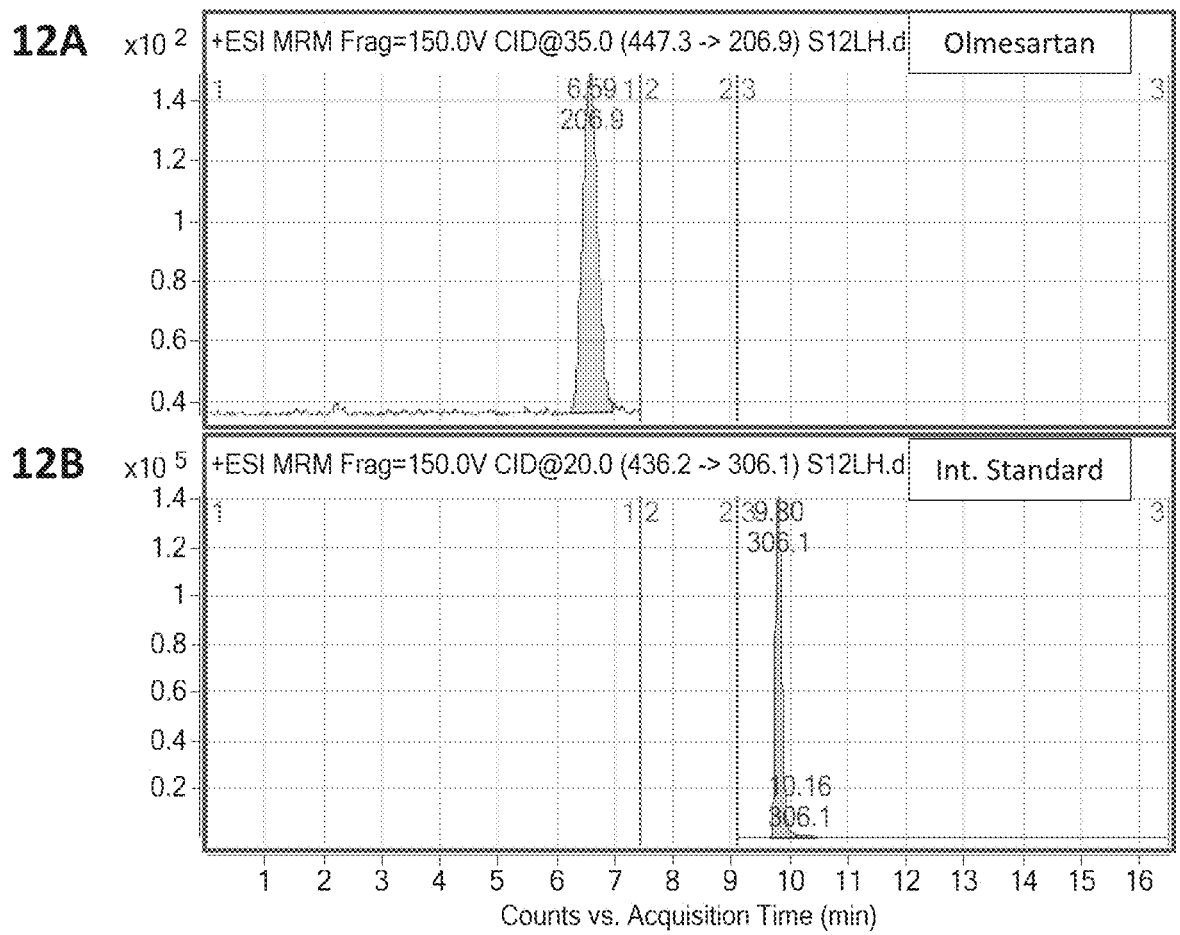
FIGS. 12A and 12B show a representative MRM transition in chromatograms of olmesartan in hepatic homogenate.

The chromatographic separation was performed on Agilent Eclipse Plus C18, 3.5 μm, 4.6×100 mm column (Agilent Technology; Palo Alto Calif., USA), maintained at 25±2° C. The mobile system for the analysis of OLM was composed of acetonitrile, A: water containing 0.05% w/v formic acid, B. From zero to 4 min, 25% A, switched to 65% A at 4.1 min. Representative MRM transition chromatograms of olmesartan and internal standard in plasma are shown in FIGS. 11A and 11B and in hepatic homogenates in FIGS. 12A and 12B.

The sample extraction and analysis were done applying the procedure published by Liu et al. in human plasma and urine (Liu et al. 2010; J Chromatog B 878(9-10):743-748), with certain modifications. In brief, separately a volume of 200 μL of plasma sample and 200 μL of the homogenate was transferred to a screw-capped test tube, mixed with 100 μL internal standard solution (valsartan, 100 ng/μL) and 700 μL acetonitrile. The prepared mixture was vortexed for 1 min, and then centrifuged at 5300 rpm for 10 min. An aliquot of about 200 μL of the clear supernatant was transferred to a total recovery autosampler vial, and a volume of 5 μL was injected for LC-MS/MS-DAD analysis. The calibration curve for olmesartan was assessed using free-drug-plasma and free drug homogenate as a calibration matrix. The stock solution of olmesartan and valsartan (InSt) were prepared separately by dissolving 10 mg of each in acetoinitril to obtain a concentration of 1 mg/mL. A series of calibrator working solutions of olmesratan were prepared from its stock solutions applying serial dilution technique using acetonitril as diluting solvent. The calibration solutions were prepared by spiking separately the plasma free drug and free drug homogenate with olmesartan solutions to give a concentration spanning the range of 1.0 to 8000.0 ng/mL of olmesartan and a fixed concentration of InSt 10 μg/mL. The calibrated solutions were extracted and analyzed by the developed method. The peak area ratios of olmesartan to InSt were found to be linear in the concentration range, 1.0 to 8000 ng/mL of olmesartan.

The olmesartan concentrations in both plasma and hepatic homogenate showed dose-dependent increases with OL & OH and with OLZMS and OHZMS. But while the OL and OH achieved higher levels in plasma and lower levels in liver homogenate, the OLZMS and OHZMS showed the reverse indicating a significant hepatic distribution. The ratio between hepatic and plasma concentrations was the greatest with OHZMS with significant differences from other treatments, as shown in Table 3.

TABLE 3

The ratio of the free olmesartan concentration in hepatic homogenate to that of plasma (H/P ratio) with olmesartan medoxomil low and high doses as raw drug (OL, OH) and as ZMS formula (OLZMS, OHZMS) in TAA-induced hepatic fibrosis rats (n = 8).

| Free olmesartan concentration | OL | OH | OLZMS | OHZMS |
|---|---|---|---|---|
| Plasma (ng/ml) | 9.87 ± 0.39 | 11.51 ± 0.42$^a$ | 3.14 ± 0.26$^b$ | 4.61 ± 0.27$^{a,b}$ |
| Hepatic homogenate (ng/g) | 0.83 ± 0.10 | 21.71 ± 0.63$^d$ | 26.24 ± 0.84$^{c,d}$ | 51.39 ± 1.88$^d$ |
| H/P ratio | 0.09 ± 0.01 | 1.90 ± 0.09$^e$ | 8.72 ± 0.67$^g$ | 11.34 ± 0.58$^{f,g}$ |

Data are expressed as mean ± SEM.
$^a$: $P < 0.05$: OH vs. OL (=0.013) and OHZMS vs. OLZMS,
$^b$: $P < 0.001$: OLZMS, OHZMS vs. OL, OH,
$^c$: $P < 0.05$: OLZMS vs. OH (=0.035),
$^d$: $P < 0.001$: OH, OLZMS, OHZMS vs. OL and OHZMS vs. OH, OLZMS,
$^e$: $P < 0.05$: OH vs. OL (=0.044),
$^f$: $P < 0.01$: OHZMS vs. OLZMS (=0.002),
$^g$: $P < 0.001$: OLZMS, OHZMS vs. OL, OH.

Size plays an important part in determining the bio-fate of nanoparticles in the body. Without being bound to theory, very small particles (<10 nm) can be rapidly cleared from the systemic circulation via renal filtration, while particles with size >200 nm have the potential to become entrapped inside the organs of reticuloendothelial system (RES). The surface decoration of nanoparticles with PEG, a flexible, neutral, and hydrophilic polymer, forms a barrier-like layer that sterically hinders the surface of the original nanoparticle. Other than steric hindrance, it confers a hydrophilic neutral attribute to the surface of nanoparticles that works as a layer opposing the interaction of the nanoparticles surface and other materials (e.g., opsonins and proteins). This provides efficient protection and long-circulation properties to PEGylated nanoparticles. PEG-PLGA allows many medications that have low water solubility, short half-life, and vulnerably easily hydrolyzed by the endogenous enzyme a chance to improve their delivery abilities with a significant elongation in their residence and is thus useful in the invention. The hydrophobic nature of zein and excellent biocompatibility allows its use to design and sustain the release of loaded drugs. Zein exhibits better absorbability and lower toxicity than synthetic nanomaterials and has the added advantage of achieving sustained drug release. Furthermore, it has been suggested that encapsulation of drugs in zein nanoparticles improves liver targeting (Lai et al. 2011; *Internat J Pharmaceu* 404(1-2):317-323 and Algandaby et al. 2016; *J Biomed Nanotech* 12(9):1746-1757). The ZMS shown in FIG. 1 differs from the prior art by including amphiphilic molecules with zein and is able to encapsulate both hydrophilic and hydrophobic drugs. Since OM is highly, hydrophobic, it is carried within the bilayer bounding the ZMS nanostructure. A hydrophilic drug of interest can be encapsulated within the inner core of the ZMS, which is a zone of hydrophilicity.

The examples of the invention demonstrate that OM-ZMS induces antifibrotic activity in liver fibrosis. In a model of human hepatic fibrosis, TAA-induced liver damage in rats was evidenced by the elevation of plasma levels of ALT and AST as well as elevation of hepatic contents of IL-6, TNF-α, and MDA, and a decline of hepatic GSH content and confirmed by the histopathological liver damage and duodenal alterations. Among the treatment groups of OL, OH, OLZMS and OHZMS, all treatments except OL significantly reversed these changes with varying degrees. The OHZMS group showed the best improvement with significant differences from other treatment groups and a non-significant difference from the normal control group, thus demonstrating the efficacy of OM-ZMS when OM is at the higher end of the range of concentration in the ZMS.

Inflammatory cytokines that are elevated during fibrogenesis activate the NF-κB and TGF-β, which are considered as the main mediators of fibrogenesis because they enhance conversion of HSCs into myofibroblasts. The conversion of HSC to myofibroblast is a critical step for stimulating synthesis and impeding degradation of the ECM, thus providing a mechanism for the accumulation of fibrotic tissue and concomitant loss of parenchymal cells in the liver.

Olmesartan medoxomil (1 mg/kg/day) given orally to bile duct-ligated fibrotic rats, significantly reduced the liver hydroxyproline content, mRNA expression of collagen, α-smooth muscle actin, and plasma levels of TGF-β suggesting that OM improved liver fibrosis. In addition, the activated HSCs were found to express AT1 receptors which, on stimulation by Ang II, induced collagen synthesis and upregulated the profibrogenic cytokines and TGF-β in rat activated HSCs. OM suppressed these fibrogenic responses in the activated HSCs indicating antifibrotic effects. The fibrogenic actions of AT II/AT1R pathway include induction of proliferation, collagen formation, and expression of the profibrogenic cytokines and TGF-β in the activated HSCs (Kurikawa et al. 2003; *Brit J Pharmacol* 139(6):1085-1094). The invention differs from this study because Kurikawa gave only one dose of raw OM (1 mg/kg/day) for two weeks starting 7 days after bile duct ligation operation (from Day 7) to Day 20 after the bile duct ligation. The improvement with this small dose given early after operation and only for two weeks indicates that the OM interfered with the complete process of development of hepatic fibrosis indicating that such effect is preventive, but does not demonstrate a therapeutic effect that can be used for treating chronic hepatic fibrosis. In addition, Kurikawa did not test any nanoformulation of OM. In contrast, the model of TAA-induced liver fibrosis in 8 weeks followed by treatment for another 8 weeks after full development of fibrosis provides a model of reversing chronic hepatic fibrosis. OM-ZMS (low and high) were administered and found to increase the concentration of olmesartan in the liver. In addition, duodenal sections were examined to detect indication of sprulike enteropathy, if any and to check effect of the OM-ZMS treatment of hepatic fibrosis-associated duodenal alterations.

The level of cAMP in hepatic tissues plays an important role in protecting against damaging fibrosis during late phase of inflammation. The increases in cAMP inhibit the formation of ECM components, inhibit fibroblast function and proliferation, and stimulate their death. In fructose-fed rats, TNF-α levels were significantly higher and cAMP levels in the soleus muscle were significantly lower than in control rats. OM (0.1 mg/kg/day) increased cAMP and reduced TNF-α (Yamaguchi et al. 2005; *Hypertens Res* 28(9):773).

Other research has attempted to provide formulations of OM to improve it bioavailability, efficacy and safety. For example, Nooli et al. showed that solid lipid nanoparticles (SLNs) used as a vehicle for oral delivery of OM revealed 2.3-fold increase in relative bioavailability of olmesartan compared to that of raw OM drug (Nooli et al. 2017; *Drug Dev Indust Pharm* 43(4):611-617) and also the OM-SLNs increased the oral bioavailability of olmesartan with twofold over that of OM-nanosuspension in rats (Veebrbrahma et al. 2018; *Artif Cell Nanomed Biotech* 46(1):126). In addition, when compared with the oral tablet of OM, the OM-loaded SLNs showed a higher drug concentration in plasma, a larger area under the curve, and a more improved oral bioavailability (Okorie et al. 2017; *J Chem Pharm Res* 9(8):64-72). Another study aimed at development of capsular dosage form of surface-adsorbed nanoemulsion (NE) of OM so as to overcome the limitations associated with handling of liquid NEs without affecting their pharmaceutical efficacy (Singh et al. 2012; *Aaps Pharm* 13(4):1212-1211). Moreover, the self-microemulsifying drug delivery system (SMEDDS), a lipophilic formulation of OM, increased its oral bioavailability and more efficiently reduced hypertension than the raw OM in rats. Interestingly, SMEDDS formulation did not cause sprue-like enteropathy or diarrhea during three weeks of treatment possibly by reducing the contact of OM with the intestine (Komesli et al. 2019; *Drug Dev Indus Pharm*:1-14). The nano-formulations used in these studies differ from the ZMS of the invention in that none of those in the prior art use zein in combination with a phospholipid and a PEG-polymer. The novel nanoformulation of the invention produces OM-ZMS with a decreased particle size that enhances its oral bioavailability and improves its pharmacodynamic profile.

Occurrence of sprue-like enteropathy or diarrhea was not observed with treatment of OM-ZMS during the eight weeks of treatment. While it remains possible that this was due to the rare nature of such a side effect, the duodenal changes observed in the TAA-treated rats were similar to those associated with liver cirrhosis in human. These changes occurred in all TAA-fibrotic rats in the positive control group, which did not receive any OM, and were not ameliorated in rats receiving OL. All doses of OM except OL significantly reversed these changes with varying degrees and the OHZMS group exhibited the best improvement with a nearly normal picture. This improvement demonstrates that these alterations are most probably linked to liver fibrosis and are not a manifestation of OM-induced sprue-like enteropathy. The detected duodenal changes included edema, vascular congestion, increased cellular infiltration, and irregularly distributed and distorted microvilli. Previously it has been reported that chronic oral ingestion of TAA causes hepatic and small intestinal alterations similar to those that usually occur with human cirrhosis (Ortega et al. 1997; *Digest Diseas Sci* 42(8):1715-1723). Also, the duodenum of cirrhotic patients showed duodenitis, atrophy, and occasional vascular malformations (Vigneri et al. 1991; *Front Pharmacol* 6:303). In addition, histologic changes have been reported in the intestinal mucosa in patients with liver cirrhosis such as edema, vascular congestion, marked distended intercellular space, increased cellular infiltration. Ultrastructural abnormalities were also seen including irregularly distributed microvilli which were distorted, shortened, and swollen with mitochondrial and nuclear changes. It is unclear whether these changes are due to increased intestinal permeability or to bacterial translocation, which are frequently found in these cirrhotic patients Such et al. 2002; *Euro J Gastroent Hepat* 14(4):376-371). In rats with methotrexate-induced intestinal mucositis, pretreatment with OM (0.5, 1.0, or 5.0 mg/kg) decreased inflammatory infiltration, vascular congestion, ulcerations, and hemorrhagic areas, as well as decreased concentrations of myeloperoxidase, IL-1β, and TNF-α levels indicating an anti-inflammatory activity. However, OM caused enteropathy characterized by diarrhea, weight loss, and decreased sucrose activity (de Araujo et al. 2015; *Biologi Pharmceut Bull* 38(5):746-752). A single injection of TAA (40 mg/kg i.p.) in mice exerted intestinal injury in form of necrosis in jejunum and ileum with or without mucosal denudation, but the duodenum remained intact. The explanation is unclear, but it may be due to enterohepatic circulation of toxic metabolites of TAA with relative sparing of the duodenum proximal to the ampulla, need for the pancreatic proteases to cause intestinal injury, or better conservation of the splanchnic blood flow to the duodenum (Caballero et al. 2001; *Gut* 48(1):34-40). In addition, Caballero et al. administered only one injection of 40 mg/kg TAA, suggesting only an acute onset of downstream effects. This contrasts with the protocol of Example 4 of the invention, wherein 200 mg/kg TAA was administered twice weekly for 8 weeks to induce a model of chronic liver fibrosis.

To determine whether the OM-ZMS nanoformulations achieved higher concentrations in the liver than the identical dose of standard OM, the free concentration of olmesartan (the active moiety) was measured in plasma and liver homogenate. Generally-speaking, drugs exist in plasma and tissues as two parts, free (unbound) and bound to proteins and lipids. The free part is the active form and is also the form available for clearance and drug interactions. The free drug concentration at the therapeutic site of action is the part that can exert effects. The partition coefficient (Kp,uu) is the ratio of unbound drug concentration in tissue to that in plasma and it is the best indicator of the extent of tissue distribution (Thanga Mariappan et al. 2013; *Cur Drug Metab* 14 (3):324-340). Under passive diffusion theory, the free drug concentration in a non-eliminating tissue is equal to that in plasma at PK steady-state (Kp,uu=~1). The free drug concentrations in plasma can be easily determined and are usually used as surrogates for the tissue drug concentrations. However, there are conditions which can lead to disequilibrium between free drug concentrations in plasma and tissues (Kp,uu is more or less than 1) such as use of drugs that are substrates for uptake and/or efflux tissue transporters, use of prodrugs that are activated in tissues, or use of nanoformulations as vehicles for drugs. However, it is often easier to determine the drug in plasma when the active drug is quickly formed from the prodrug by carboxylesterases in gut or plasma, which is the case with OM in the current study. In addition, the OM-ZMS nanoformulation increases drug concentration in liver, thus nanoparticles make significant differences between tissue and plasma concentrations. The OM-ZMS are well-tolerated with fewer systemic side effects due to the uptake and accumulation in liver, which significantly increases the hepatic distribution. This is in contrast to standard OM, which is mainly distributed in the extracellular space with low volume of distribution due to its highly lipophilic nature.

This is in agreement with Gorain et al. (2014; *Colloids Surf B:Biointerfaces* 115:286-294), who showed that nanoemulsification improves oral bioavailability with elongated PD activity of OM in Wistar rats. Olmesartan in plasma peaked in 0.5 h, followed by elimination phase and the in vivo studies with the nanoemulsion showed better and extended control of experimentally induced hypertension with 3-fold decrease of the conventional dose. Moreover, in Wistar rats, the biodistribution study showed significantly higher tissue (brain and liver) concentrations of olmesartan at 0.5, 2.0 and 8.0 h following oral administration of the nanoemulsion compared to the aqueous OM suspension. Also, the OM nanoemulsion was found to be safe as detected during the 28-days sub-chronic toxicity study Gorain et al., (2014) *Reg Tox and Pharmacol* 82:20-31).

Other nano-formulations of OM are known, such as those found in US20120148637, which teaches a crystalized form of OM, and others, such as US20160303102, which teaches preparation of nanoparticles of OM in a cellulose polymer matrix. US20180250227 teaches methods for preparing sodium or potassium alginate carriers for OM. US20110143993 teaches targeted lipid-polymeric nanoparticles, including a soybean lecithin and peptide-conjugated distearolylphosphatidylethanoloamine-PEG shell and PLGA encapsulating paclitaxel. WO2016013031A1 discloses a liposomal formulation which comprises one or more phospholipids, one or more steroidal lipids, and one or more hydrophilic polymer derivatized lipids. CN102138899B and CN103040777B each teach a liposome comprising phophatidylcholine and PEG-polymers. However, none of these formulations include zein to produce zeinmersomes encapsulating OM for treatment of chronic liver fibrosis and its associated duodenal changes. Zein exhibits better absorbability and lower toxicity than synthetic nanomaterials and has the added advantage of achieving sustained drug release. In a preferred formulation, the ZMS of the invention contains a phospholipid, PEG-PLGA and zein. The invention further includes methods for administering OM-ZMS as a treatment of liver fibrosis and duodenal changes associated with liver fibrosis.

In addition, the invention differs from the disclosure found in US20200048218, which is related to non-alcoholic fatty liver disease (NAFLD). High fat diet (HFD) was used to induce hepatic steatosis in mouse models. US20200048218 discloses that olmesartan is an AT1 blocker and that it improves HFD-induced hepatic steatosis (abnormal retention of fat within a cell or organ) by inhibiting ASK1 and that a reduction of ASK1 also reduces hepatic fibrosis. The model used is not one of chronic liver fibrosis, such as the method disclosed in Example 4 to induce fibrogenesis in rats with TAA (200 mg/kg, ip) injected twice weekly for eight weeks. Moreover, many agents showed potent antifibrotic effects in vitro, but unfortunately exerted minor effects in vivo due to insufficient concentrations around the HSCs and even caused adverse effects occur due to affection of other non-target cells. Hundreds of compounds prevented development of experimental hepatic fibrosis, but there is no data about their ability to reverse already-established chronic hepatic fibrosis. Thus, it is more sensible if the anti-fibrotic candidates are tested in models of established fibrosis. This is the case in our work. In addition, US20200048218 is silent about any use of a nanoformulation of olmesartan medoxomil (OM). The OM-ZMA showed more favorable efficiency in reversing hepatic fibrosis and this was confirmed by detection of higher concentration of olmesartan (the active moiety) in hepatic tissue compared with that of the raw OM. Thus, the therapeutic effect of OM-ZMS in reversing hepatic fibrosis is more effective compared with the raw OM. While the low dose of raw OM failed to exert any effect, the same identical dose of OM-ZMS exerted an improvement. Also, the high dose of OM-ZMS (OHZMS group) exerted more significant improvement than the same identical dose of the raw OM. Rat tissue sections were examined for presence of spru-like enteropathy. No sprue-like enteropathy or diarrhea was detected during the eight weeks of treatment, however, duodenal changes similar to those occurring with liver cirrhosis in human were observed, suggesting that it is a valid model of chronic hepatic fibrosis. These changes occurred in all TAA-fibrotic rats including the positive control group that did not receive any OM and, interestingly, all doses of OM except OL significantly reversed these changes with varying degrees. The OHZMS treatment produced the greatest degree of improvement with a nearly normal picture. Thus, the histopathological alterations observed in TAA-treated rats were linked to liver fibrosis rather than OM-induced sprue-like enteropathy.

In conclusion, OM has unique properties compared with the other ARBs. In addition to blocking AT1R, it has an inverse agonist activity and no antagonistic effects on AT2R. Also, it upregulates ACE2, stimulates the tissue-protective ACE2/Ang-(1-7)/Mass receptor pathway, inhibits ACE, and decreases plasma level of angiotensin II. The OM-ZMS of the invention, compared with the same identical doses of the standard OM, produced a higher hepatic drug concentration, exerted a more efficient antifibrotic effect, and improved liver fibrosis-associated duodenal changes more effectively. The OM-ZMS are well-tolerated with fewer systemic side effects, compared with the standard OM, even with the significantly higher hepatic distribution that is achieved. Accordingly, the OM-ZMS are an effective and well-tolerated nano-vehicle formula for oral administration of OM for treatment of chronic hepatic fibrosis and its associated duodenal changes.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A pharmaceutical composition of a drug encapsulated in a zeinmersome, comprising a mixture of zein, an amphiphilic copolymer and at least one phospholipid,
   wherein the zein, the amphiphilic copolymer and the at least one phospholipid form a lipid bilayer, and
   wherein the lipid bilayer encapsulates a suitable amount of the drug within a nanosized zeinmersome vesicle bounded by the lipid bilayer,
   wherein the size range of the zeinmersome is 95 to 200 nm in diameter.

2. The pharmaceutical compostition of claim 1, wherein the amphiphilic copolymer is poly (ethylene glycol) methyl ether-block-poly (lactide-co-glycolide) (PEG-PLGA).

3. The pharmaceutical composition of claim 1, wherein the at least one phospholipid is selected from the group consisting of phosphatidylcholine, phosphatidic acid, phosphatidylethanolamine, phosphatidylserine, phosphatidylglycerol, phosphatidylinositol, phosphatidylinositol phosphate, phosphatidylinositol bisphosphate and phosphatidylinositol trisphosphate.

4. The pharmaceutical composition of claim 1, wherein the drug is olmesartan, olmesartan medoxomil or (5-methyl-2-oxo-1,3-dioxol-4-yl)methyl 5-(2-hydroxypropan-2-yl)-2-propyl-3-[[4-[2-(2H-tetrazol-5-yl)phenyl]phenyl]methyl] imidazole-4-carboxylate.

5. The pharmaceutical composition of claim 4, wherein the drug present in the zainersome is at a concentration in the range of 3% to 15% w/w.

* * * * *